US012491024B2

(12) United States Patent

Duan

(10) Patent No.: US 12,491,024 B2

(45) Date of Patent: Dec. 9, 2025

(54) PORTABLE HAIR REMOVAL APPARATUS

(71) Applicant: Shenzhen Yangwo Electronic Co., Ltd., Shenzhen (CN)

(72) Inventor: Dejin Duan, Shenzhen (CN)

(73) Assignee: SHENZHEN YANGWO ELECTRONIC CO., LTD., Shenzhen (CN)

( * ) Notice: Subject to any disclaimer, the term of this patent is extended or adjusted under 35 U.S.C. 154(b) by 798 days.

(21) Appl. No.: 17/739,201

(22) Filed: May 9, 2022

(65) Prior Publication Data

US 2022/0346871 A1 Nov. 3, 2022

Related U.S. Application Data

(63) Continuation of application No. PCT/CN2020/072556, filed on Jan. 16, 2020.

(30) Foreign Application Priority Data

Aug. 9, 2019 (CN) ......................... 201921303582.5
Aug. 9, 2019 (CN) ......................... 201921303584.4
(Continued)

(51) Int. Cl.
*A61B 18/18* (2006.01)
*A61B 18/00* (2006.01)
*A61N 5/06* (2006.01)

(52) U.S. Cl.
CPC ..... *A61B 18/18* (2013.01); *A61B 2018/00011* (2013.01); *A61B 2018/00476* (2013.01); *A61B 2018/1807* (2013.01); *A61N 5/0617* (2013.01)

(58) Field of Classification Search
CPC .......... A61B 18/18; A61B 2018/00466; A61B 18/20; A61B 18/203; A61B 2090/034;
(Continued)

(56) References Cited

U.S. PATENT DOCUMENTS 6,273,885 B1 8/2001 Koop et al.
9,302,118 B2 * 4/2016 Weckwerth .......... A61N 5/0616
(Continued)

FOREIGN PATENT DOCUMENTS

CN 102935012 A 2/2013
CN 204233213 U 4/2015
(Continued)

OTHER PUBLICATIONS

International Search Report of PCT Patent Application No. PCT/CN2020/072556 issued on May 6, 2020.

*Primary Examiner* — Carl H Layno
*Assistant Examiner* — Dhrasti Snehal Dalal
(74) *Attorney, Agent, or Firm* — Andrew C. Cheng

(57) ABSTRACT

The present disclosure relates generally to a portable hair removal apparatus The portable hair removal apparatus-includes a hair removal mechanism for contacting the skin to remove hair, and a housing. The housing defines an accommodating space, and the hair removal mechanism is accommodated therein. The hair removal mechanism includes a light-exit portion for emitting light irradiated to the hair to be removed, and a contact portion. The contact portion is exposed from the accommodating space and disposed in a light-emitting direction of the light-exit portion. The contact portion includes a light-transmitting crystal disposed in the light-emitting direction of the light-exit portion, and the light-transmitting crystal is in contact with the skin. In the field of portable hair removal devices, the light-transmitting crystal is provided on the contact portion, to contact the skin for cold compress, reducing the burning sensation on the skin caused by the light-exit portion.

14 Claims, 13 Drawing Sheets

(30) Foreign Application Priority Data

| | | |
|---|---|---|
| Aug. 9, 2019 | (CN) | 201921303915.4 |
| Aug. 9, 2019 | (CN) | 201921314110.X |
| Jan. 10, 2020 | (CN) | 202020065851.5 |

(58) Field of Classification Search

CPC .......... A61B 90/04; A61B 2018/00005; A61B 2018/00452; A61B 2017/00752; A61N 2005/0644; A61N 5/0617; A61N 5/067; A45D 26/00

See application file for complete search history.

(56) References Cited

U.S. PATENT DOCUMENTS

| | | | | |
|---|---|---|---|---|
| 2010/0069898 | A1* | 3/2010 | O'Neil | A61B 18/203 607/90 |
| 2012/0165682 | A1 | 6/2012 | Keeney et al. | |
| 2012/0165800 | A1* | 6/2012 | Keeney | A61B 18/203 606/9 |
| 2013/0197495 | A1 | 8/2013 | Koifman et al. | |
| 2018/0117355 | A1* | 5/2018 | Loupis | A61N 5/0616 |
| 2022/0192745 | A1* | 6/2022 | Pan | A61B 18/18 |

FOREIGN PATENT DOCUMENTS

| | | | | | |
|---|---|---|---|---|---|
| CN | 105521566 | A | | 4/2016 | |
| CN | 207755373 | U | | 8/2018 | |
| CN | 207804371 | U | | 9/2018 | |
| CN | 207804372 | U | | 9/2018 | |
| CN | 207980186 | U | | 10/2018 | |
| CN | 208598513 | U | | 3/2019 | |
| CN | 213606854 | U | * | 7/2021 | A45D 26/00 |
| WO | WO-2018185773 | A1 | * | 10/2018 | A61B 18/203 |

* cited by examiner

PORTABLE HAIR REMOVAL APPARATUS

TECHNICAL FIELD

The present disclosure relates generally to the technical field of portable hair removal devices, and more particularly to a portable hair removal apparatus.

BACKGROUND

Hair removal devices usually include optical hair removal devices, such as laser hair removal devices and IPL (Intense Pulse Light) hair removal devices. However, in the existing optical hair removal devices, due to the large heat generated by light, the laser exposure during laser hair removal can cause a burning sensation to the skin.

Portable hair removal devices have appeared in the existing hair removal devices, but the heat dissipation efficiency of them is insufficient, still causing a large burning sensation during hair removal.

SUMMARY

In order to overcome the problem of insufficient heat dissipation efficiency in the existing portable hair removal devices, the present disclosure provides a portable hair removal apparatus.

To solve the technical problem, an embodiment of the present disclosure provides a portable hair removal apparatus. The portable hair removal apparatus includes a hair removal mechanism for contacting the skin to remove hair, and a housing which defines an accommodating space for the hair removal mechanism to be accommodated therein. The hair removal mechanism includes a light-exit portion for emitting light irradiated to the hair to be removed, and a contact portion which is exposed from the accommodating space and is disposed in a light-emitting direction of the light-exit portion. The contact portion includes a light-transmitting crystal disposed in the light-emitting direction of the light-exit portion, and the light-transmitting crystal is in contact with the skin.

Preferably, the portable hair removal apparatus further includes a heat dissipation mechanism accommodated in the accommodating space. The heat dissipation mechanism includes a blowing member, a heat dissipation channel and a heat dissipation assembly. The heat dissipation assembly is disposed between the blowing member and the heat dissipation channel, or the heat dissipation assembly is disposed at a side of the heat dissipation channel close to the blowing member.

Preferably, the housing is provided with a first vent and a second vent which are communicated with the accommodating space. The blowing member is disposed corresponding to the first vent. The heat dissipation assembly includes a heat dissipation member and at least one heat conduction member. The heat dissipation member is disposed between the blowing member and the heat dissipation channel, or the heat dissipation member is disposed at the side of the heat dissipation channel close to the blowing member. One end of the heat dissipation channel is communicated with the second vent, the other end thereof is connected to the heat dissipation member. One end of the at least one heat conduction member is in contact with the heat dissipation member, the other end thereof is in contact with at least one side of the hair removal mechanism. The blowing member pushes air flow between the first vent and the second vent.

Preferably, the blowing member includes a first air inlet and a first air outlet. The first air inlet is disposed corresponding to the first vent. The first air outlet is disposed corresponding to the heat dissipation member. The heat dissipation channel includes a second air inlet and at least one second air outlet. The second air inlet is disposed corresponding to the heat dissipation member. The at least one second air outlet is communicated with the second vent.

Preferably, the heat dissipation mechanism further includes a sealing element. The sealing element is sleeved on a side of the heat dissipation member close to the heat conduction member, to seal a gap between the heat dissipation channel and the heat dissipation member.

Preferably, the heat conduction member includes a condensing section and a heat dissipating section which are oppositely disposed. The condensing section is connected to the heat dissipation member. The heat dissipating section is connected to at least one side of the light-transmitting crystal. The condensing section is connected to a side of the light-transmitting crystal close to the heat dissipation member.

Preferably, the number of the heat conduction member is at least two. The at least two heat conduction members are respectively disposed at opposite sides of the heat dissipation member. The heat conduction member is U-shaped or imitated U-shaped.

Preferably, a hollow spacer element is positioned between the light-exit portion and the light-transmitting crystal.

Preferably, the heat dissipation mechanism further includes at least one semiconductor refrigeration sheet disposed between the light-transmitting crystal and the heat conduction member. The at least one semiconductor refrigeration sheet includes a refrigeration surface and a heat dissipation surface which are oppositely disposed. The refrigeration surface is in contact with the side of the light-transmitting crystal. The heat dissipation surface is in contact with the heat dissipating section. The refrigeration surface is in contact with at least one side corresponding to a wide side or a long side of the light-transmitting crystal.

Preferably, the contact portion includes a collar sleeved on a side of the housing, and a first sensing member positioned in the collar for sensing conductors.

Preferably, the contact portion further includes a limiting member and a contact member. The limiting member is sleeved on an outer side of the light-transmitting crystal to fasten the light-transmitting crystal. The contact portion is disposed on the outer side of the light-transmitting crystal to cover an area between the collar and the light-transmitting crystal. At least one side of the limiting member and/or the contact member close to the light-transmitting crystal is provided with a limiting portion protruding toward the light-transmitting crystal. The light-transmitting crystal defines a groove corresponding to and matching the limiting portion.

Preferably, the portable hair removal apparatus further includes a control module. The control module is electrically connected to the light-exit portion. The first sensing member includes at least two sensing sections. The at least two sensing sections are positioned in the collar, and each sensing section is electrically connected to the control module. The collar is formed on a peripheral side of the at least two sensing sections. The distance between each sensing section and a side of the collar away from the light-exit portion is 0.2 mm-2 mm. The distance between two adjacent sensing sections is 3 mm-30 mm.

Preferably, the light-exit portion includes a light tube, an optical filter and a reflective member, which are disposed in the heat dissipation channel. The heat dissipation channel is provided with a light-exit opening at a side close to the contact portion. The light tube is positioned in the heat dissipation channel, for emitting light irradiated to the hair to be removed through the light-exit opening. The optical filter is disposed in the light-emitting direction of the light tube. The reflective member is disposed in a direction opposite to the light-emitting direction.

Preferably, the portable hair removal apparatus further includes a converting head detachably connected to the contact portion. A converting opening is defined in the converting head corresponding light-exit opening. The diameter of the converting opening is different from that of the light-exit opening. The converting head further includes a second sensing member sleeved on a peripheral side of the light-exit opening, for sensing the conductors. The converting head includes a metal surface at a side close to the light-transmitting crystal. The metal surface is electrically connected to the second sensing member. When the converting head is connected to the hair removal mechanism, the first sensing member senses the metal surface.

Preferably, the portable hair removal apparatus further comprises a Hall switch positioned at a side in the housing close to the hair removal mechanism, and the converting head includes a first magnetic member. When the converting head is connected to the hair removal mechanism, the Hall switch senses the first magnetic member to control light emitting of the hair removal mechanism.

Compared with the prior arts, the portable hair removal apparatus provided in the present disclosure have the following beneficial effects.

In the field of portable hair removal devices, the light-transmitting crystal is provided on the contact portion, to contact the skin for cold compress, thereby reducing the burning sensation on the skin caused by the light emitted by the light-exit portion.

The blowing member, the heat dissipation channel and the heat dissipation assembly are provided. The heat dissipation assembly is disposed between the blowing member and the heat dissipation channel, or the heat dissipation assembly is disposed at a side of the heat dissipation channel close to the blowing member, which improves the heat dissipation efficiency of the heat dissipation assembly to the hair removal mechanism, and improves the space utilization rate in the housing. The volume of the portable hair removal apparatus is further reduced while ensuring the heat dissipation efficiency therein.

The heat dissipation member and the heat conduction member are provided. The heat dissipation member is disposed at the first air outlet of the blowing member, which improves the heat dissipation efficiency of the heat dissipation member based on the larger wind pressure of the first air outlet, further improves the heat dissipation efficiency to the hair removal mechanism by the heat conduction member, reduces the burning sensation caused by hair removal and improves user experience of the product.

The number of the provided second air outlets is increased. The air exhaust efficiency in the heat dissipation channel is improved, and the space utilization rate in the housing is further improved.

The sealing member is provided to seal the gap between the heat dissipation channel and the blowing member, which prevents the air blew by the blowing member from leaking and further improves the heat dissipation efficiency to the hair removal mechanism.

One end of the heat conduction member is connected to an end of a side of the light-transmitting crystal close to the heat dissipation member, the other end of the heat conduction member is connected to the heat dissipation member. That is, the heat conduction member is disposed on the end of the side of the light-transmitting crystal away from the light-emitting direction, whereby the light-transmitting crystal can protrude out of the housing, which enables the size of the contact portion to be smaller, and increases the area ratio of the light-transmitting crystal on the side surface of the contact portion in contact with the skin. Therefore, during hair removal, the smaller size of the contact portion facilitates the user to observe the hair removal situation in real time without removing the apparatus to observe, which avoids the problem of inconvenient observation and operation caused by the contact portion being too large, and improves the user experience.

At least two heat conduction members are provided. The at least two heat conduction members are respectively disposed at the opposite sides of the heat dissipation member, whereby the heat dissipation member can dissipate heat from the two heat conduction members more evenly, which improves the heat dissipation efficiency.

The hollow spacer element is positioned between the optical filter and the light-transmitting crystal. The spacer element seals the area between the light-transmitting crystal and the light-exit portion, to prevent the air at opposite sides of the light-exit portion and/or the light-transmitting crystal from liquefying, which further improves the light-emitting quality and prevents the liquid from flowing out, to protect the internal electronic components.

The semiconductor refrigeration sheet is disposed between the light-transmitting crystal and the heat conduction member. The semiconductor refrigeration sheet directly dissipates heat from the light-transmitting crystal, which further improves the heat dissipation efficiency to the light-transmitting crystal. Meanwhile, the semiconductor refrigeration sheet is in contact with one side corresponding to the wide side y of the light-transmitting crystal, whereby the contact portion maintains the size in the direction of the wide side y, the contact portion has a smaller width while the semiconductor refrigeration sheet is provided, and the contact portion can be adapted to more hair removal operations of skins with narrow areas.

The first sensing member is provided to sense conductors. The portable hair removal apparatus is triggered to emit light only when the portable hair removal apparatus is really in contact with the surface to be hair-removed, which avoids ineffective light emitting when the portable hair removal apparatus is not in contact with the skin, saves electricity, improves the safety of hair removal, and prevents damage to external objects caused by ineffective light emitting.

The limiting member is provided. At least one side of the limiting member and/or the contact member close to the light-transmitting crystal is provided with a limiting portion protruding toward the light-transmitting crystal. The light-transmitting crystal defines a groove corresponding to and matching the limiting portion. The limiting portion can be placed in the groove, whereby the limiting portion can abut against the groove to fasten the light-transmitting crystal and prevent the light-transmitting crystal from falling.

The first sensing member is configured as at least two sensing sections. The at least two sensing sections are positioned in the collar, whereby the user's skin to be hair-removed needs to be simultaneously sensed by each sensing section, and then the light-exit portion can be controlled by the switch to emit light, to ensure that the user needs to completely contact the hair removal window of the portable hair removal apparatus with the skin during the process of hair removal, the multiple sensing sections can be used to achieve electrical conduction, which avoids ineffective light emitting caused by the user accidentally touching a part of the collar, and further saves electricity and avoids unsafe use. Further, when the skin is completely and simultaneously electrically conducted to the multiple sensing sections, the skin to be hair-removed completely covers the light-transmitting crystal, to ensure that the light emitted from the light-transmitting crystal is completely irradiated on the skin to be hair-removed, thereby avoiding ineffective light emitting caused by the user accidentally touching a part of the collar, and preventing damage caused by the light irradiated from the non-covered part of the light-transmitting crystal, which improves the safety of hair removal. The collar is formed at the peripheral side of the at least two sensing sections, whereby the collar covers the at least two sensing sections, to seal the multiple sensing sections, which prevents wrong conduction of the first sensing member caused by the liquid formed on the surface of the sensing section due to temperature changes, and improves the safety of hair removal. The distance between each sensing section and the side of the collar away from the light-exit portion is 0.2 mm-2 mm. When the collar is in contact with the skin to be hair-removed, it is ensured that the sensing section and the skin to be hair-removed are within a sensing range, which improves the sensitivity of the sensing section. The distance between two adjacent sensing sections is 3 mm-30 mm, which prevents the distance between two adjacent sensing sections from being too short, avoids electrical conduction caused by the user accidentally touching the area between two adjacent sensing sections, and further improves the safety of hair removal.

The converting head detachably connected to the contact portion is provided. The diameter of the converting opening is different from that of the light-exit opening, whereby users can add converting heads based on needs, to adapt to the hair removal requirements for different parts, especially smaller parts, such as lips, fingers and other smaller areas to be hair-removed.

The second sensing member is disposed in the converting head. When the converting head is installed for hair removal, the second sensing member senses the conductor to control the light emitting.

The first magnetic member is disposed in the converting head. The Hall switch is provided. When the converting head is connected to the hair removal mechanism, the Hall switch senses the first magnetic member and is closed, which avoids the electrical conduction caused by the first sensing member sensing the converting head when the converting head is installed. The Hall switch can sense the connection of the converting head, to control the light emitting of the light-exit portion.

NUMERICAL REFERENCE IDENTIFICATION

1. portable hair removal apparatus;
11. housing; 111. first vent; 112. second vent; 113. second magnetic member;
12. heat dissipation mechanism; 121. blowing member; 1211. first air inlet; 1212. first air outlet; 122. heat dissipation channel; 1221. second air inlet; 1222. second air outlet; 123. heat dissipation assembly; 1231. heat dissipation member; 12311. connection piece; 12312. heat sink; 1232. heat conduction member; 12321. condensing section; 12322. heat dissipating section; 124. sealing element; 125. semiconductor refrigeration sheet; 1251. refrigeration surface; 1252. heat dissipation surface; 1253. positive wire; 1254. negative wire; 126. spacer element; 1261. protrusion;
13. hair removal mechanism; 131. light-exit portion; 1311. light tube; 1312. optical filter; 1313. reflective member; 1314. light-exit opening; 1315. flow opening; 132. contact portion; 1321. light-transmitting crystal; 13211. groove; 1322. collar; 1323. contact member; 1324. first sensing member; 13241. sensing section; 1325. limiting member; 13251. limiting portion;
14. switch; 15. power supply;
16. converting head; 161. first magnetic member; 162. converting opening; 163. second sensing member; 164. metal surface;
17. Hall switch; 18. circuit board.

DETAILED DESCRIPTION

In order to make the objectives, technical solutions, and advantages of the present disclosure clearer, the present disclosure is further described in detail below with reference to the accompanying drawings and embodiments. It should be understood that the specific embodiments described herein are provided for illustration only, and not for the purpose of limiting the disclosure.

Figure 1:
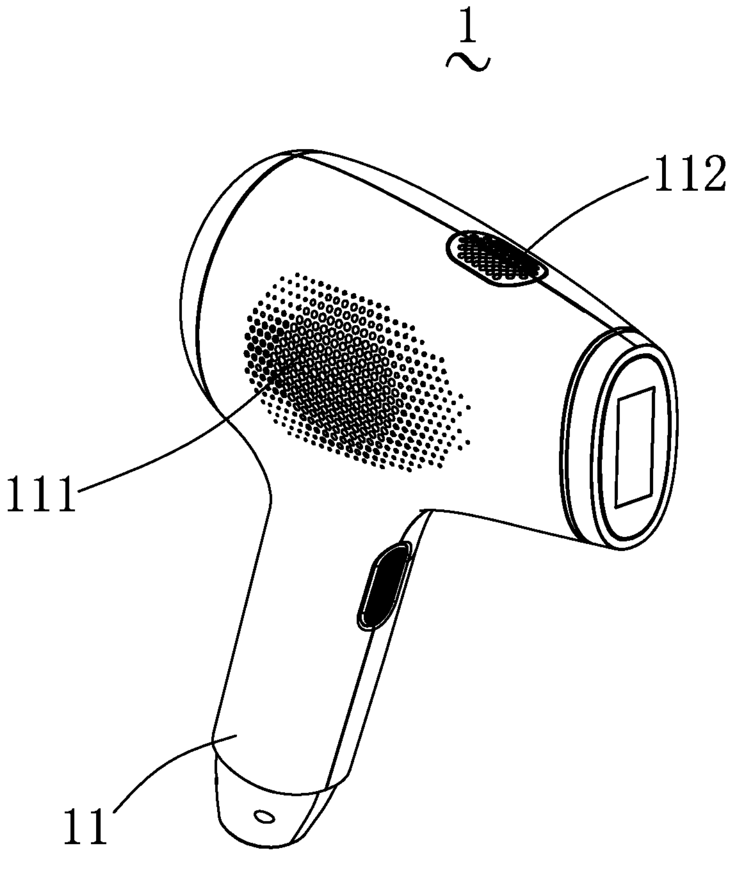
FIG. 1 is an overall schematic diagram of a portable hair removal apparatus according to a first embodiment of the present disclosure.
Figure 2:
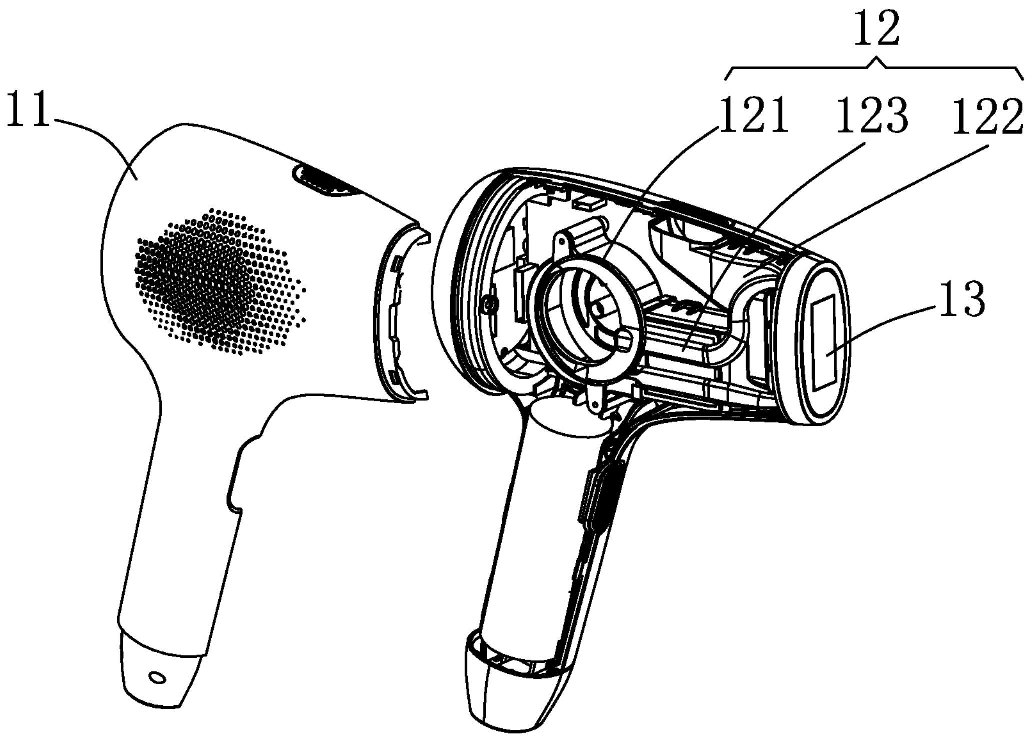
FIG. 2 is a partial exploded schematic diagram of the portable hair removal apparatus according to the first embodiment of the present disclosure.

Referring to FIG. 1 and FIG. 2, an embodiment of the present disclosure provides a portable hair removal apparatus 1. The portable hair removal apparatus 1 includes a housing 11, a heat dissipation mechanism 12 and a hair removal mechanism 13. The housing 11 defines an accommodating space where the heat dissipation mechanism 12 and the hair removal mechanism 13 are accommodated. The hair removal mechanism 13 is configured to remove hair by emitting light in contact with the skin. The heat dissipation mechanism 12 is configured to dissipate heat from the hair removal mechanism 13.

Referring to FIG. 1 and FIG. 2 again, specifically, the heat dissipation mechanism 12 includes a blowing member 121, a heat dissipation channel 122 and a heat dissipation assembly 123. The heat dissipation assembly 123 is disposed between the blowing member 121 and the heat dissipation channel 122, or the heat dissipation assembly 123 is disposed at a side of the heat dissipation channel 122 close to the blowing member 121.

The housing 11 is provided with a first vent 111 and at least one second vent 112 which communicate the accommodating space. The blowing member 121 is disposed corresponding to the first vent 111. An end of the heat dissipation channel 122 is communicated with the at least one second vent 112. The blowing member 121 pushes the air flow between the first vent 111 and the at least one second vent 112.

It can be understood that, the at least one second vent 112 can be disposed on at least one side of the housing 11 in a vertical direction and/or a horizontal direction, so as to improve the air outlet efficiency. For example, in this embodiment, the number of the second vent 112 is one, and the second vent 112 is disposed on a side of the housing 11 in the vertical direction (as shown in FIG. 1).

Figure 3:
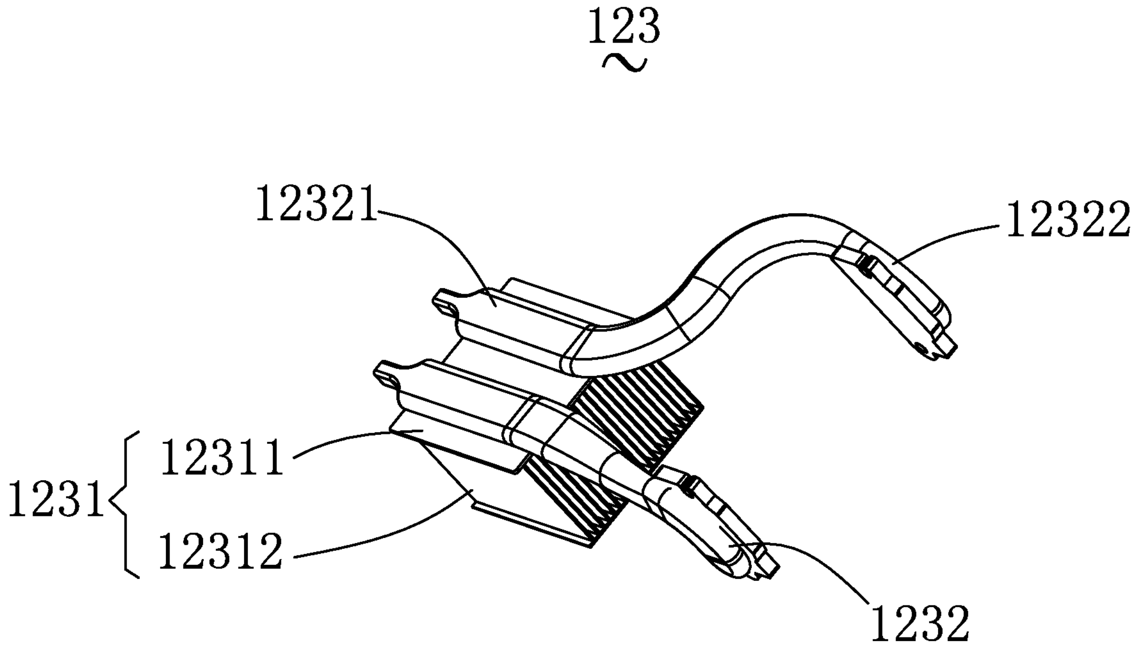
FIG. 3 is a schematic diagram of a heat dissipation assembly according to the first embodiment of the present disclosure.
Figure 4:
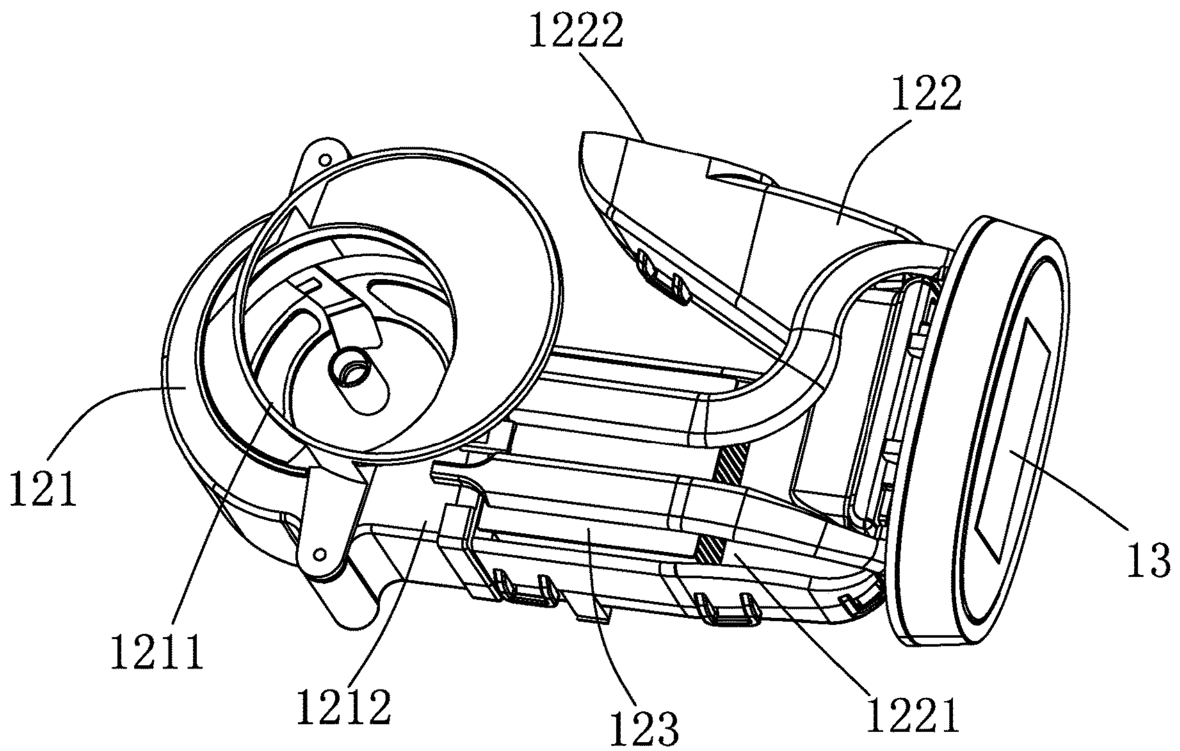
FIG. 4 is a schematic diagram of the heat dissipation assembly, a heat dissipation channel and a blowing member according to the first embodiment of the present disclosure.

Referring to FIG. 3 and FIG. 4, the heat dissipation assembly 123 includes a heat dissipation member 1231 and a heat conduction member 1232. The heat dissipation member 1231 is disposed between the blowing member 121 and the heat dissipation channel 122, or the heat dissipation member 1231 is disposed at the side of the heat dissipation channel 122 close to the blowing member 121. One end of the heat dissipation channel 122 is communicated with the at least one second vent 112, the other end of the heat dissipation channel 122 is connected to the heat dissipation member 1231. One end of the heat conduction member 1232 is in contact with the heat dissipation member 1231, the other end of the heat conduction member 1232 is in contact with at least one side of the hair removal mechanism 13, for dissipating heat from the hair removal mechanism 13. Specifically, the heat conduction member 1232 includes a condensing section 12321 and a heat dissipating section 12322 which are oppositely disposed. The condensing section 12321 is in contact with the heat dissipation member 1231. The heat dissipating section 12322 is in contact with the hair removal mechanism 13.

It can be understood that, the heat conduction member 1232 is a heat pipe, and the hair removal mechanism 13 is heat-conducted through the heat pipe. The heat conduction member 1232 can also be made of other thermally conductive materials such as copper sheet, vapor chamber, etc., as long as the heat conduction member 1232 can conduct heat of the hair removal mechanism 13, which is not limited herein. For example, in this embodiment, the heat conduction member 1232 is the heat pipe, but this is not a limitation of this solution.

It can be understood that, the number of the heat conduction member 1232 can be one, two or more, and the number can be increased or decreased based on needs. For example, in this embodiment, the number of the heat conduction member 1232 is two, and each heat conduction member 1232 is in contact with the side of the hair removal mechanism 13 to dissipate heat.

Referring to FIG. 3 and FIG. 4 again, optionally, the heat dissipation member 1231 includes at least one connection piece 12311 and at least one heat sink 12312. The at least one heat sink 12312 is in contact with one side of the at least one connection piece 12311. The heat conduction member 1232 is in contact with the other side of the at least one connection piece 12311. For example, in this embodiment, the number of the heat sink 12312 can be twenty. The twenty heat sinks 12312 are arranged successively, and each heat sink 12312 is disposed perpendicular to the at least one connection piece 12311. There is a gap between two adjacent heat sinks 12312, whereby the air blew from the blowing member 121 can flow through the heat dissipation member 1231 through the gap, thereby dissipating heat from the heat dissipation member 1231. Further, the heat dissipation member 1231 is in contact with the heat conduction member 1232, whereby the heat dissipation member 1231 can dissipate heat from the heat conduction member 1232.

That is, the heat conduction member 1232 can dissipate heat from the hair removal mechanism 13.

It can be understood that, the heat dissipation member 1231 can be formed by welding multiple heat sinks 12312 and one connection piece 12311. Compared with the traditional integrated heat dissipation fins, the heat sink 12312 of the heat dissipation member 1231 can have a smaller thickness, whereby under the same size, the heat dissipation member 1231 can connect more heat sinks 12312, to increase the surface area of the heat dissipation member 1231 and improve the heat dissipation efficiency. The heat dissipation member 1231 can also be directly configured as a heat dissipation fin, which is not limited herein.

It can be understood that, the connection piece 12311 and the heat sink 12312 can be any one or more of metal heat-conducting materials such as copper, iron, aluminum, etc., which can be selected based on needs and will not be repeated here.

Referring to FIG. 1 and FIG. 4, the blowing member 121 includes a first air inlet 1211 and a first air outlet 1212. The first air inlet 1211 is disposed corresponding to the first vent 111. The first air outlet 1212 is connected to the heat dissipation member 1231.

The heat dissipation channel 122 includes a second air inlet 1221 and at least one second air outlet 1222. The second air inlet 1221 is connected to the heat dissipation member 1231. The at least one second air outlet 1222 is communicated with the at least one second vent 112.

Figure 5:
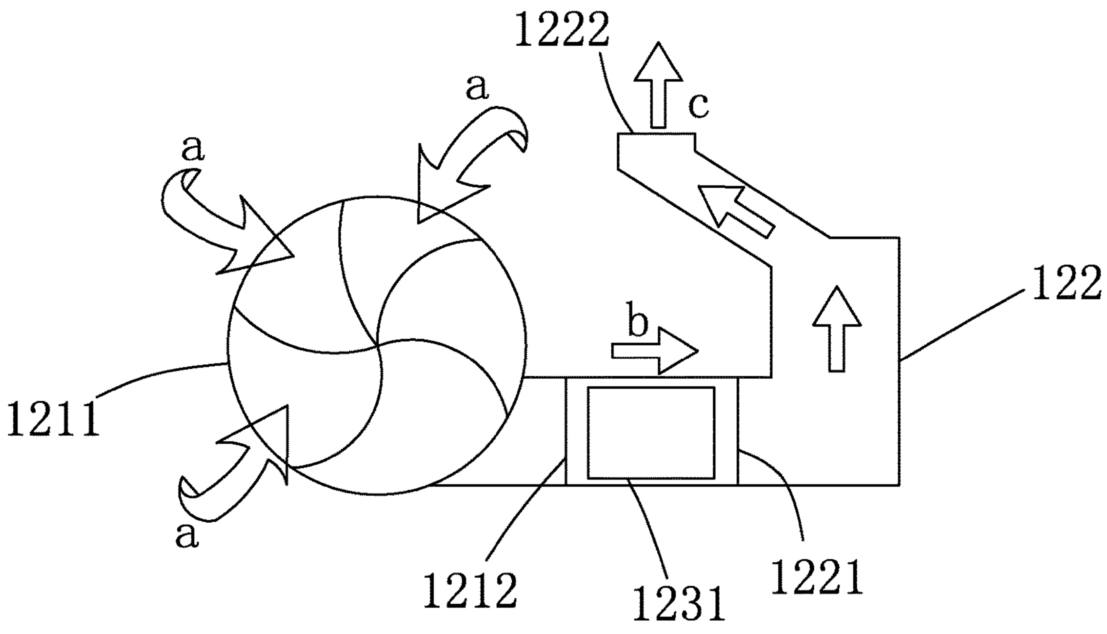
FIG. 5 is a schematic diagram of the direction of the internal air duct in the portable hair removal apparatus according to the first embodiment of the present disclosure.

Referring to FIG. 1, FIG. 4 and FIG. 5, the air flow direction of the heat dissipation mechanism 12 is as follows: when the blowing member 121 is turned on, the blowing member 121 sucks external air into the first air inlet 1211 (as shown in the direction a in FIG. 5), and exhausts it to the heat dissipation member 1231 through the first air outlet 1212, thereby dissipating heat from the heat dissipation member 1231 through the flow of external air; meanwhile, the external air flowing through the heat dissipation member 1231 enters into the heat dissipation channel 122 through the second air inlet 1221 (as shown in the direction b in FIG. 5), and flows out through the second air outlet 1222 (as shown in the direction c in FIG. 5), that is, the external air is exhausted out of the housing 11 from the second vent 112 through the second air outlet 1222, so as to realize the air flow between the first vent 111 and the second vent 112.

It can be understood that, the blowing member 121 can be a blower, which sucks external air into the blowing member 121 through the first air inlet 1211, and exhausts it through the first air outlet 1212. According to the characteristics of the blower, it can be known that the wind pressure of the first air outlet 1212 is greater than that of the first air inlet 1211, whereby the air flow rate of the first air outlet 1212 is greater than that of the first air inlet 1211, which further improves the heat dissipation efficiency of the heat dissipation member 1231.

Figure 6:
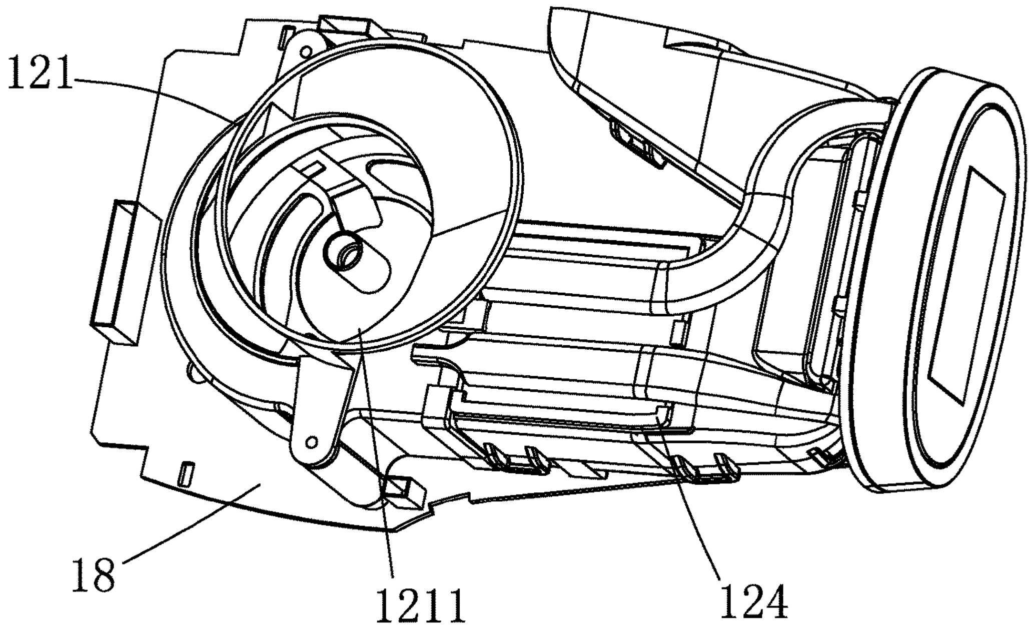
FIG. 6 is a schematic diagram of the position of a sealing element in the portable hair removal apparatus according to the first embodiment of the present disclosure.

Optionally, referring to FIG. 4 and FIG. 6, the heat dissipation mechanism 12 further includes a sealing element 124. The sealing element 124 is sleeved on a side of the heat dissipation member 1231 close to the heat conduction member 1232, so as to seal the gap between the heat dissipation channel 122 and the heat dissipation member 1231.

Specifically, the sealing element 124 has a hollow structure. The sealing element 124 can be sleeved on the peripheral side of the heat dissipation member 1231 close to the heat conduction member 1232, at least that the sealing element 124 is flush with a side of the heat dissipation channel 122 close to the heat conduction member 1232, so as to seal the gap between the heat dissipation channel 122 and the heat dissipation member 1231.

It can be understood that, the heat dissipation member 1231 is positioned at a side of the heat dissipation channel 122 close to the blowing member 121, whereby there is a gap between the heat dissipation channel 122 and the heat dissipation member 1231. That is, the air can flow out through the gap when flowing through the heat dissipation member 1231, which reduces the air flow rate flowing into the heat dissipation channel 122, and reduces the heat dissipation efficiency to the hair removal mechanism 13. The sealing member 124 is provided to seal the gap, which prevents the air from leaking and improves the heat dissipation efficiency to the hair removal mechanism 13.

Optionally, referring to FIG. 6 again, a circuit board 18 is positioned away from the first air inlet 1211. The circuit board 18 includes a control module (not shown) corresponding to the blowing member 121, whereby the air generated by the blowing member 121 can dissipate heat from the control module.

Figure 7:
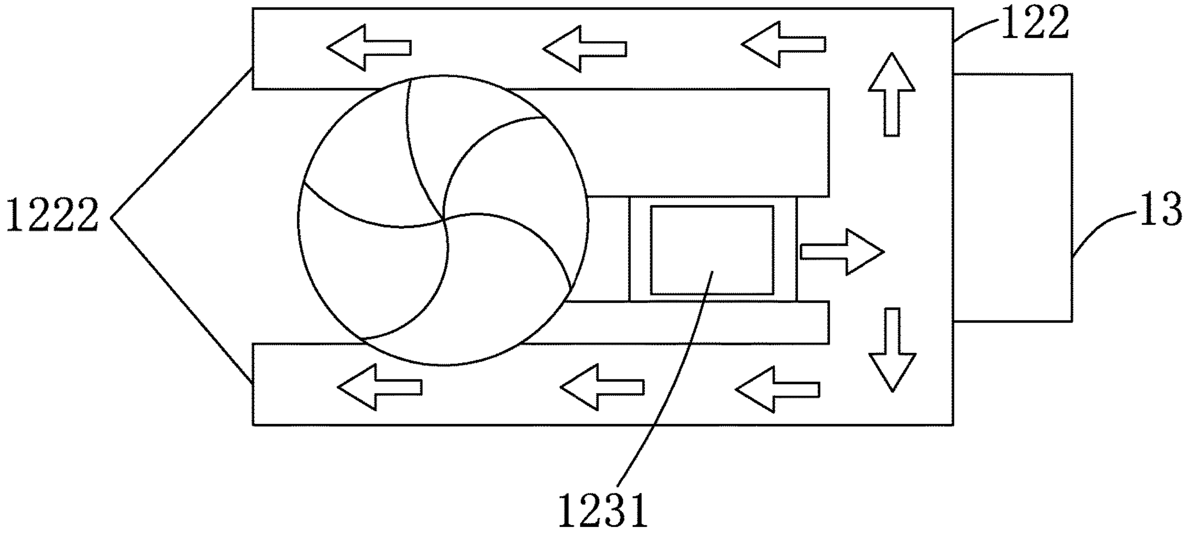
FIG. 7 is a schematic diagram of two second air outlets provided in the heat dissipation channel in the portable hair removal apparatus according to the first embodiment of the present disclosure.

Optionally, referring to FIG. 1 and FIG. 7, the number of the second air outlet 1222 is two, and the two second air outlets 1222 are disposed at a side of the housing 11 away from the hair removal mechanism 13. It can be understood that, the heat dissipation channels 122 corresponding to the two second air outlets 1222 are respectively disposed at two sides of the heat dissipation member 1231 and the blowing member 121, and the air is exhausted out from the side of the housing 11 away from the hair removal mechanism 13. By increasing the number of the second air outlet 1222, the air exhaust efficiency in the heat dissipation channel 122 is improved, while the space utilization rate in the housing 11 is further improved.

Figure 8:
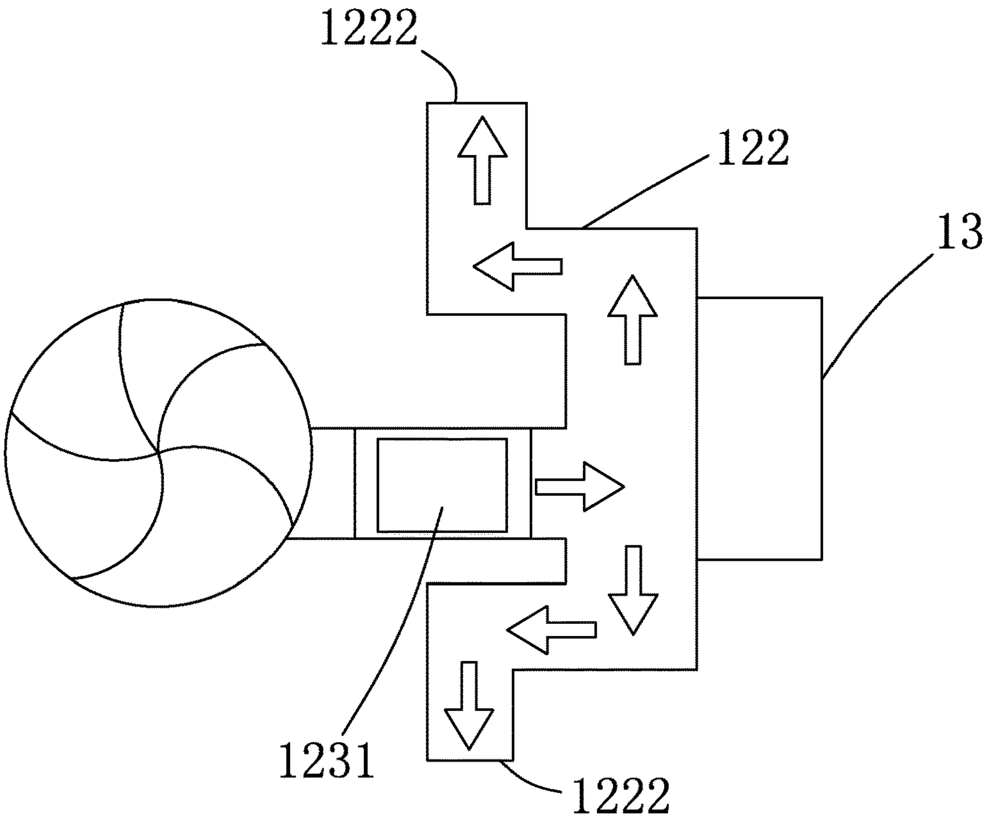
FIG. 8 is another schematic diagram of two second air outlets provided in the heat dissipation channel in the portable hair removal apparatus according to the first embodiment of the present disclosure.

Optionally, referring to FIG. 1 and FIG. 8, the number of the second air outlet 1222 is two, and the two second air outlets 1222 are disposed at opposite sides of the housing 11. The two second air outlets 1222 can also be disposed at other positions of the housing 11, which will not be repeated here.

Figure 9:
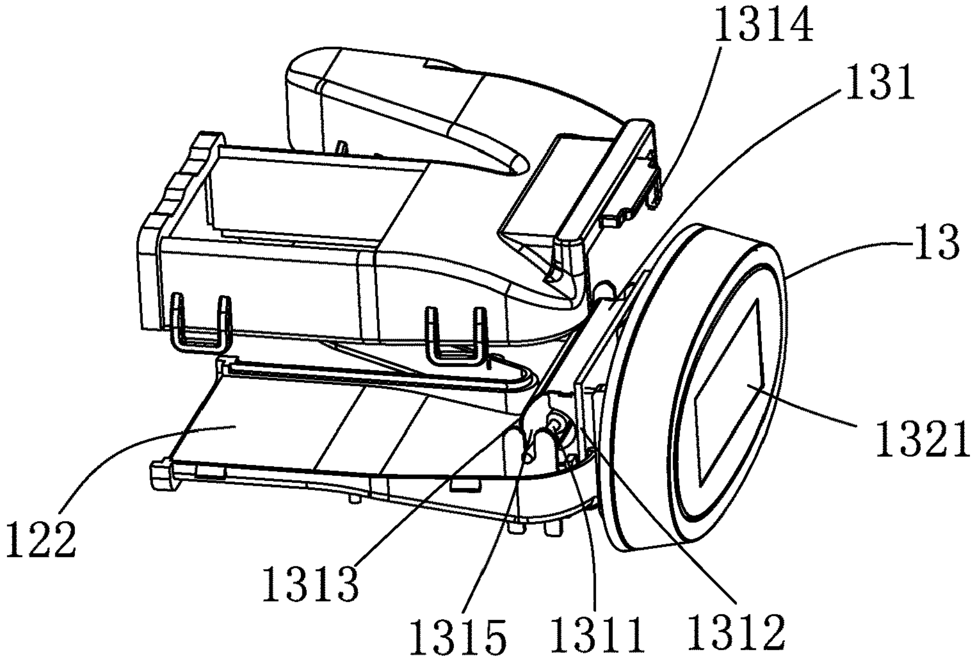
FIG. 9 is a schematic diagram of a light-exit portion in the portable hair removal apparatus according to the first embodiment of the present disclosure.
Figure 10:
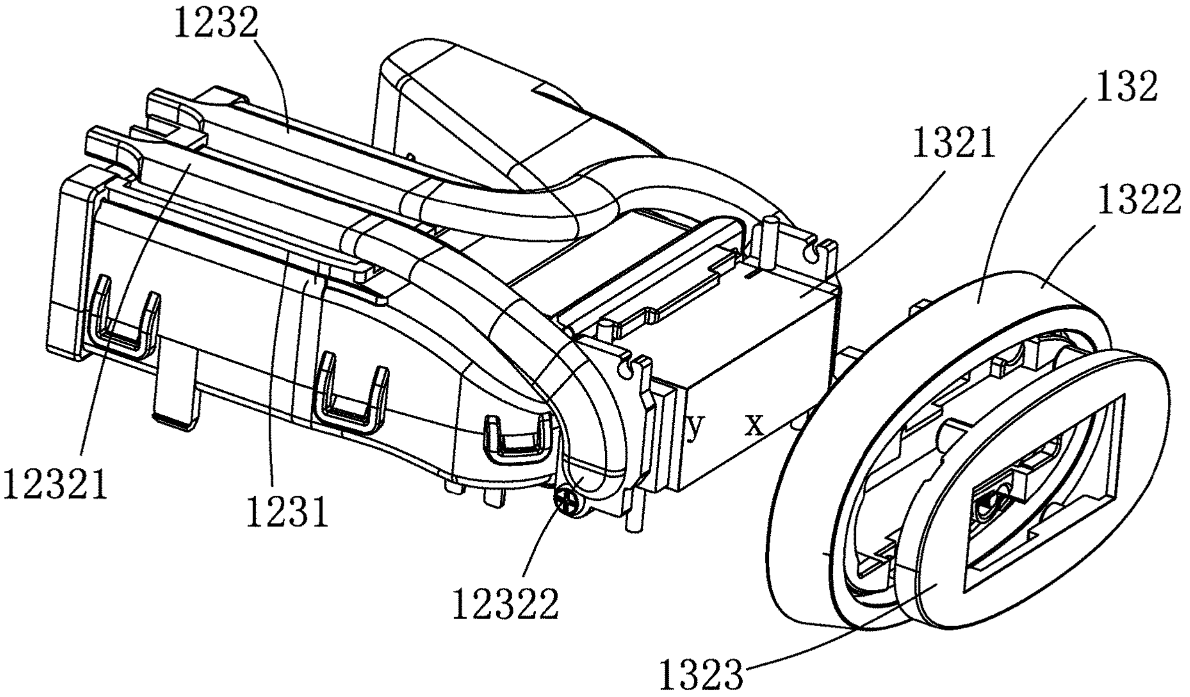
FIG. 10 is a schematic diagram of a contact portion in the portable hair removal apparatus according to the first embodiment of the present disclosure.

Referring to FIG. 9 and FIG. 10, the hair removal mechanism 13 includes a light-exit portion 131 and a contact portion 132. The light-exit portion 131 is configured to emit light irradiated to the hair to be removed. The contact portion 132 is configured to contact the skin to be hair-removed.

Specifically, the contact portion 132 includes a light-transmitting crystal 1321 disposed in a light-emitting direction of the light-exit portion 131. The light-transmitting crystal 1321 is in contact with the skin for cold compress, which reduces the burning sensation on the skin caused by the light emitted by the light-exit portion 131. The light-transmitting crystal 1321 includes but not limited to any one of sapphire crystal, quartz glass, and K9 glass.

It can be understood that, the condensing section 12321 of the heat conduction member 1232 is in contact with the heat dissipation member 1231. The heat dissipating section 12322 is in contact with at least one side of the light-transmitting crystal 1321, whereby the heat conduction member 1232 can directly dissipate heat from the light-transmitting crystal 1321.

Optionally, the contact portion 132 further includes a collar 1322 and a contact member 1323. The contact member 1323 is sleeved on an outer side of the light-transmitting crystal 1321. The collar 1322 is sleeved on an outer side of the contact member 1323. The contact member 1323 is configured to cover the gap between the collar 1322 and the light-transmitting crystal 1321.

Further, the contact member 1323 can be a plastic contact member or a metal contact member. For example, when the contact member 1323 is the metal contact member, the contact member 1323 can dissipate heat from the light-transmitting crystal 1321, and the contact member 1323 is in contact with the skin, further achieving cold compress effects to the skin.

It can be understood that, the contact member 1323 is flush with a side of the light-transmitting crystal 1321 in contact with the skin, or is lower than the side thereof, so as to ensure that the light-transmitting crystal 1321 is always in contact with the skin.

Figure 11:
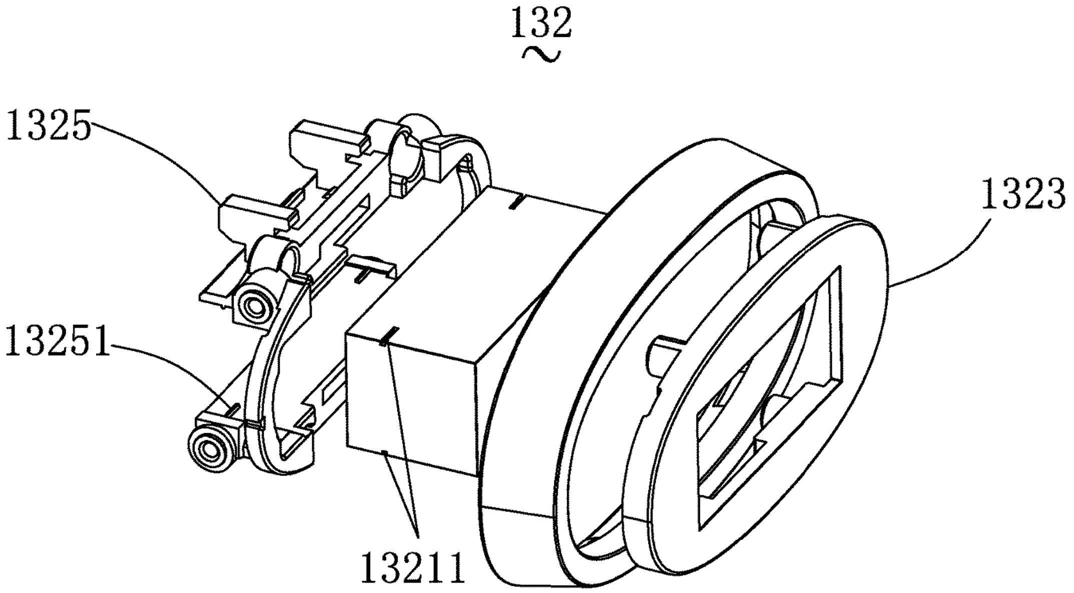
FIG. 11 is a schematic diagram of a limiting member in the portable hair removal apparatus according to the first embodiment of the present disclosure.

Referring to FIG. 11, the contact portion 132 further includes a limiting member 1325. The limiting member 1325 is sleeved on the peripheral side of the light-transmitting crystal 1321, so as to fasten the light-transmitting crystal 1321 and prevent the light-transmitting crystal 1321 from falling.

Specifically, at least one side of the limiting member 1325 and/or the contact member 1323 close to the light-transmitting crystal 1321 is provided with a limiting portion 13251 protruding toward the light-transmitting crystal 1321. The light-transmitting crystal 1321 defines a groove 13211 corresponding to and matching the limiting portion 13251. The limiting portion 13251 can be placed in the groove 13211, whereby the limiting portion 13251 can abut against the groove 13211 to fasten the light-transmitting crystal 1321.

Optionally, the number of the groove 13211 is four, and the four grooves 13211 are arranged on opposite sides of the light-transmitting crystal 1321 in a length direction x and are symmetrically arranged. Correspondingly, the number of the limiting portion 13251 is four, and the four limiting portions 13251 are disposed on a side of the limiting member 1325 corresponding to the four grooves 13211.

It can be understood that, the groove 13211 can also be at least one through-groove structure defined on the light-transmitting crystal 1321, and the limiting portion 13251 is disposed corresponding to the groove 13211. Or the groove 13211 can also be arranged on two sides of the light-transmitting crystal 1321 close to the contact member 1323 in a width direction y, and the limiting portion 13251 is disposed on a side of the contact member 1323 corresponding to the groove 13211. The groove 13211 and the limiting portion 13251 can also be disposed at other positions, as long as the limiting portion 13251 is placed in the groove 13211, whereby the limiting portion 13251 can abut against the groove 13211 to fasten the light-transmitting crystal 1321, which will not be repeated here.

Referring to FIG. 9 and FIG. 10 again, the light-exit portion 131 includes a light tube 1311, an optical filter 1312 and a reflective member 1313. The light tube 1311, the optical filter 1312 and the reflective member 1313 are disposed in the heat dissipation channel 122.

Specifically, the heat dissipation channel 122 is provided with a light-exit opening 1314 and a flow opening 1315 at a side close to the contact portion 132. The flow opening 1315 is communicated with the heat dissipation channel 122. The light tube 1311 is installed in the heat dissipation channel 122, for emitting light irradiated to the hair to be removed through a light-exit opening 1314. The optical filter 1312 is disposed in the light-emitting direction of the light tube 1311. The reflective member 1313 is disposed in a direction opposite to the light-emitting direction, whereby the light emitted by the light tube 1311 is concentrated by the reflective member 1313 and irradiated from the light-exit opening 1314, and passes through the optical filter 1312 to form a preset light and finally irradiates from the light-transmitting crystal 1321. The preset light can be irradiated to the skin to be hair-removed.

The reflective member 1313 and the optical filter 1312 cooperate to form a wind-guide channel which is communicated with the flow opening 1315, that is, the flow opening 1315 is disposed at opposite sides of the wind-guide channel. The light tube 1311 is accommodated in the wind-guide channel. The external air can flow through the wind-guide channel through the flow opening 1315, that is, the air flowing into the heat dissipation channel 122 can flow through the wind-guide channel through the flow opening 1315, to dissipate heat from the light-exit portion 131 and reduce the heat of the preset light generated by the light-exit portion 131.

Referring to FIG. 9 and FIG. 10 again, it can be understood that, the light-transmitting crystal 1321 includes a long side and a wide side (the long side x and the wide side y as shown in FIG. 10), and the length of the long side x is greater than or equal to that of the wide side y. The heat dissipating section 12322 is in contact with at least one side of the light-transmitting crystal 1321. For example, in this embodiment, the heat dissipating section 12322 is in contact with at least one side corresponding to the long side x and/or the wide side y of the light-transmitting crystal 1321, so as to realize the heat dissipation to the light-transmitting crystal 1321 through the contact between the heat conduction member 1232 and the light-transmitting crystal 1321, whereby the light-transmitting crystal 1321 has a lower temperature when in contact with the skin, which reduces the burning sensation on the skin during hair removal.

It can be understood that, in this embodiment, the heat dissipating section 12322 of the heat conduction member 1232 is in contact with at least one side corresponding to the wide side y of the light-transmitting crystal 1321. For example, two heat dissipating sections 12322 of two heat conduction members 1232 are respectively attached to two sides corresponding to the wide side y of the light-transmitting crystal 1321. Therefore, the contact portion 132 maintains the size in the direction of the wide side y, and the contact portion 132 has a smaller width while the heat conduction member 1232 is provided, whereby the contact portion 132 can be adapted to more hair removal operations of skins with narrow areas.

Figure 12:
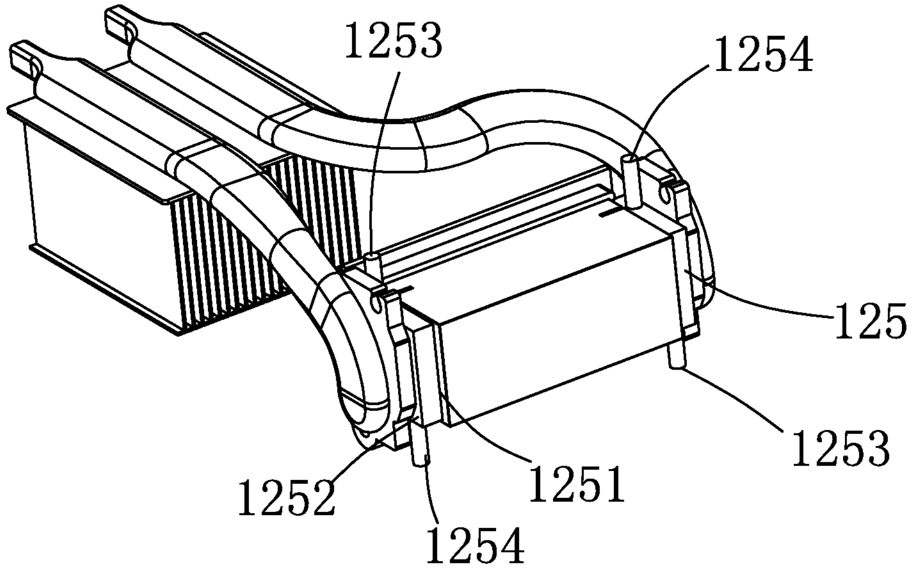
FIG. 12 is a schematic diagram of the heat dissipation assembly provided with a semiconductor refrigeration sheet in the portable hair removal apparatus according to the first embodiment of the present disclosure.

Referring to FIG. 10 and FIG. 12, optionally, the heat dissipation mechanism 12 further includes at least one semiconductor refrigeration sheet 125. The at least one semiconductor refrigeration sheet 125 is disposed between the light-transmitting crystal 1321 and the heat conduction member 1232. Specifically, the at least one semiconductor refrigeration sheet 125 includes a refrigeration surface 1251 and a heat dissipation surface 1252 which are oppositely disposed. The refrigeration surface 1251 is in contact with a side of the light-transmitting crystal 1321. The heat dissipation surface 1252 is in contact with the heat dissipating section 12322. The at least one semiconductor refrigeration sheet 125 is disposed between the light-transmitting crystal 1321 and the heat conduction member 1232, and the at least one semiconductor refrigeration sheet 125 directly dissipates heat from the light-transmitting crystal 1321, which further improves the heat dissipation efficiency to the light-transmitting crystal 1321.

It can be understood that, the at least one semiconductor refrigeration sheet 125 is in contact with at least one side corresponding to the wide side y of the light-transmitting crystal 1321. For example, in this embodiment, the number of the semiconductor refrigeration sheet 125 is two, and the two semiconductor refrigeration sheets 125 are respectively disposed at and in contact with two sides corresponding to the wide side y of the light-transmitting crystal 1321.

Therefore, the contact portion 132 maintains the size in the direction of the wide side y, and the contact portion 132 has a smaller width while the semiconductor refrigeration sheet 125 is provided, whereby the contact portion 132 can be adapted to more hair removal operations of skins with narrow areas. The two semiconductor refrigeration sheets 125 can also be disposed at and in contact with two sides corresponding to the long side x of the light-transmitting crystal 1321, as long as the two semiconductor refrigeration sheets 125 are in contact with the light-transmitting crystal 1321 to dissipate heat.

Referring to FIG. 10 and FIG. 12 again, optionally, the at least one semiconductor refrigeration sheet 125 includes a positive wire 1253 and a negative wire 1254. The positive wire 1253 and the negative wire 1254 are respectively disposed at opposite ends of the at least one semiconductor refrigeration sheet 125. The positive wire 1253 and the negative wire 1254 are respectively wound on opposite sides of the light-transmitting crystal 1321. Specifically, the two semiconductor refrigeration sheets 125 are symmetrically disposed on the opposite sides of the light-transmitting crystal 1321, whereby the positive wire 1253 of one semiconductor refrigeration sheet 125 is electrically connected to the negative wire 1254 of the other semiconductor refrigeration sheet 125 along the long side x of the light-transmitting crystal 1321, so as to connect the positive wire 1253 and the negative wire 1254 in series by winding the two semiconductor refrigeration sheets 125 on the opposite sides of the light-transmitting crystal 1321, which increases the space utilization rate and further makes the contact portion 132 have a smaller size, and the contact portion 132 can be adapted to more hair removal operations of skins with narrow areas.

Figure 13:
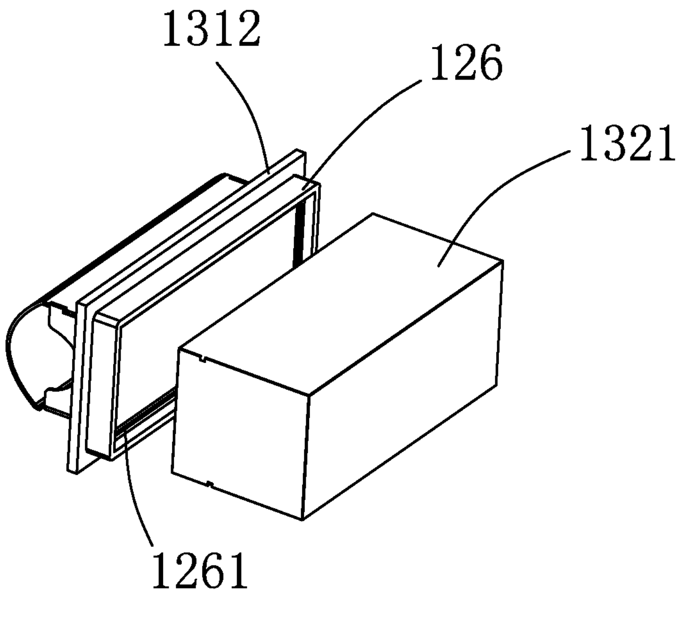
FIG. 13 is a schematic diagram of a spacer element in the portable hair removal apparatus according to the first embodiment of the present disclosure.

Referring to FIG. 13, optionally, a hollow spacer element 126 is positioned between the optical filter 1312 and the light-transmitting crystal 1321. The spacer element 126 seals the area between the optical filter 1312 and the light-transmitting crystal 1321.

It can be understood that, the spacer element 126 is provided with a protrusion 1261 at an edge of the hollow area. When the spacer element 126 is sleeved on the peripheral side of the light-transmitting crystal 1321, the protrusion 1261 can fasten a side of the light-transmitting crystal 1321 close to the optical filter 1312, whereby a vacuum is always maintained between the optical filter 1312 and the light-transmitting crystal 1321. That is, the spacer element 126 seals the area between the optical filter 1312 and the light-transmitting crystal 1321, to prevent the air at opposite sides of the optical filter 1312 and/or the light-transmitting crystal 1321 from liquefying, which further improves the light-emitting quality and prevents the liquid from flowing out, to protect the internal electronic components.

Figure 14:
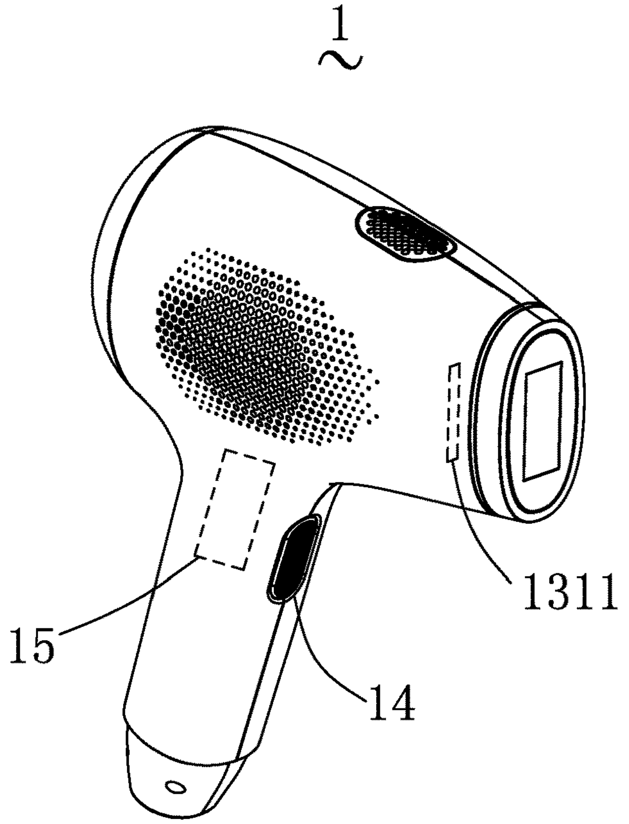
FIG. 14 is a schematic diagram of a switch and a power supply in the portable hair removal apparatus according to the first embodiment of the present disclosure.

Referring to FIG. 14, the portable hair removal apparatus 1 further includes a switch 14 and a power supply 15. The switch 14 is configured to control turning on or off the light tube 1311 to emit light. The power supply 15 is configured to supply power to the light tube 1311.

Figure 15:
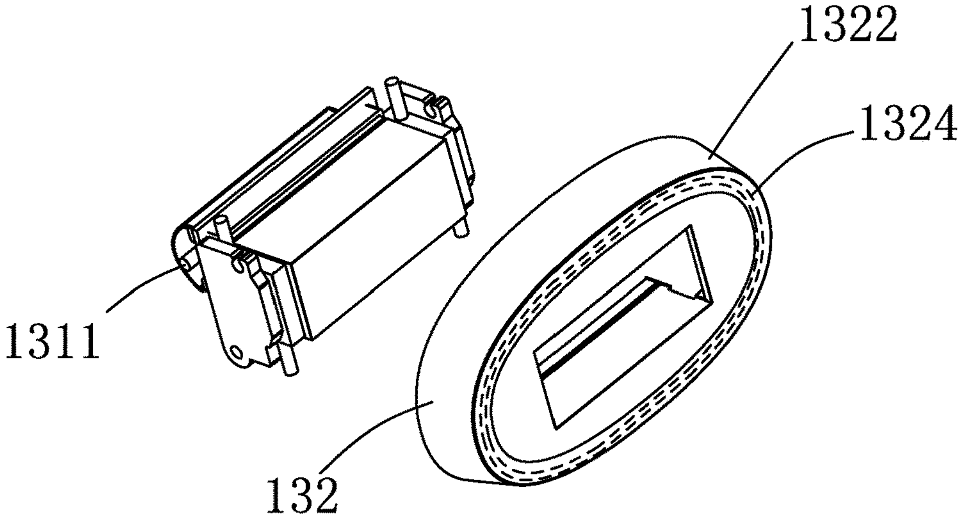
FIG. 15 is a schematic diagram of a first sensing member in the portable hair removal apparatus according to the first embodiment of the present disclosure.

Referring to FIG. 15, the contact portion 132 further includes a first sensing member 1324 (as shown by the broken lines in FIG. 15) and a control module (not shown). The first sensing member 1324 is positioned in the collar 1322 and configured to sense conductors.

It can be understood that, the first sensing member 1324 is a sensing metal sheet, such as a copper sheet or a silver sheet, which is configured to sense conductors. By bringing a conductor, such as the user's skin to be hair-removed, close to the first sensing member 1324, the capacitance of the first sensing member 1324 is changed, and a control signal is sent to the control module according to the capacitance change, to control an electrical conduction of the light tube 1311.

Specifically, the first sensing member 1324 is electrically connected to the control module, and the control module is electrically connected to the light tube 1311. When the first sensing member 1324 senses the conductor, the first sensing member 1324 is electrically conducted to the control module, whereby the control module conducts the light tube 1311 and the power supply 15. At this time, the user can control the light emitting of the light tube 1311 by the switch 14. That is, when the first sensing member 1324 senses the conductor, such as the user's skin to be hair-removed, and after the user presses the switch 14, the light tube 1311 can emit light, which avoids ineffective light emitting caused by the light tube 1311 when it is not in contact with the skin, saves electricity, improves the safety of hair removal, and prevents damage to external objects caused by ineffective light emitting.

Figure 16:
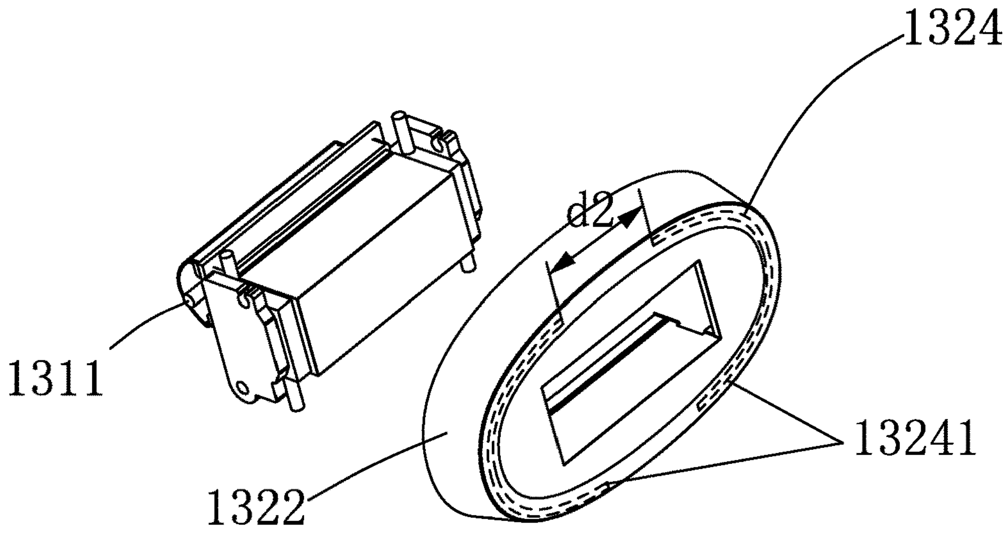
FIG. 16 is a schematic diagram of multiple sensing sections in the portable hair removal apparatus according to the first embodiment of the present disclosure.

Referring to FIG. 16, optionally, the first sensing member 1324 includes at least two sensing sections 13241. The at least two sensing sections 13241 are positioned in the collar 1322 and are respectively electrically connected to the control module. For example, in this embodiment, the number of the sensing section 13241 is two, and the two sensing sections 13241 are evenly positioned in the collar 1322. The number of the sensing section 13241 can also be three, four or more, which is not limited herein.

It can be understood that, the first sensing member 1324 is configured as multiple sensing sections 13241, whereby the user's skin to be hair-removed needs to be simultaneously sensed by each sensing section 13241, and the multiple sensing sections 13241 are simultaneously electrically conducted to the control module, whereby the control module conducts the light tube 1311 and the power supply 15. At this time, the user can control the light emitting of the light tube 1311 by the switch 14.

It can be understood that, the multiple sensing sections 13241 are provided to ensure that the skin needs to be completely and simultaneously electrically conducted to the multiple sensing sections 13241 during the process of hair removal, which avoids ineffective light emitting caused by the user accidentally touching a part of the collar, and further saves electricity. Further, when the skin is completely and simultaneously electrically conducted to the multiple sensing sections 13241, the skin to be hair-removed completely covers the light-transmitting crystal 1321, to ensure that the light emitted from the light-transmitting crystal 1321 is completely irradiated on the skin to be hair-removed, thereby avoiding ineffective light emitting caused by the user accidentally touching a part of the collar, and preventing damage caused by the light irradiated from the non-covered part of the light-transmitting crystal 1321, which improves the safety of hair removal.

Figure 17:
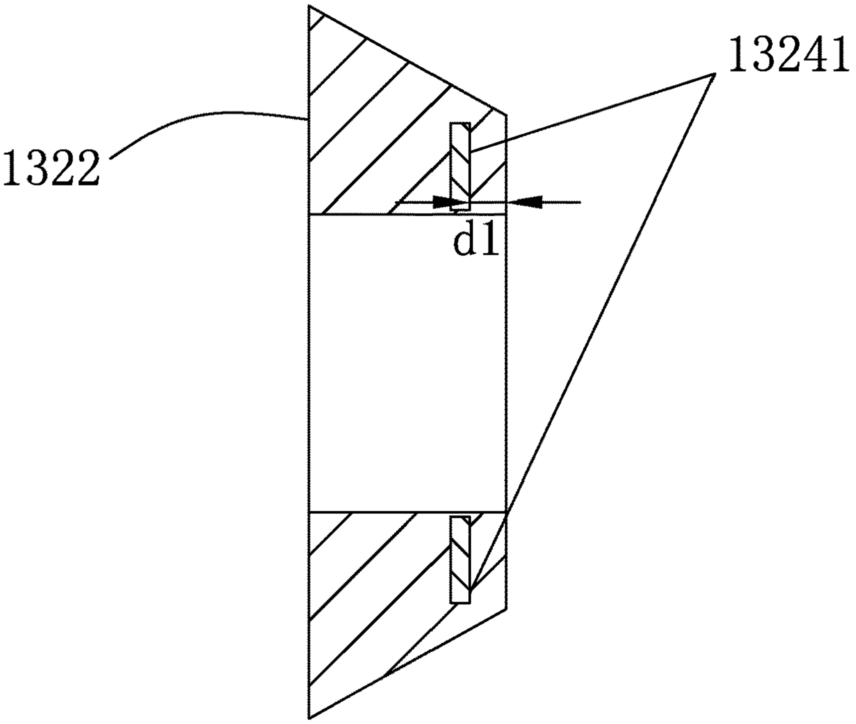
FIG. 17 is a sectional schematic diagram of a collar in the portable hair removal apparatus according to the first embodiment of the present disclosure.

Referring to FIG. 16 and FIG. 17, optionally, the collar 1322 is formed at the peripheral side of the at least two sensing sections 13241. That is, the collar 1322 is injection-molded at the peripheral side of the at least two sensing sections 13241, whereby the collar 1322 covers the at least two sensing sections 13241, to seal the multiple sensing sections 13241, which prevents wrong conduction of the first sensing member 1324 caused by the liquid formed on the surface of the sensing section 13241 due to temperature changes (the liquid will cause the sensing section 13241 to be electrically conducted), and improves the safety of hair removal.

The distance between each sensing section 13241 and the side of the collar 1322 away from the light-exit portion 131 is 0.2 mm-2 mm (for example, the distance d1 as shown in FIG. 17). When the collar 1322 is in contact with the skin to be hair-removed, it is ensured that the sensing section 13241 and the skin to be hair-removed are within a sensing range, which improves the sensitivity of the sensing section 13241.

Further, the distance between two adjacent sensing sections 13241 is 3 mm-30 mm (for example, the distance d2 as shown in FIG. 16), which prevents the distance between two adjacent sensing sections 13241 from being too short, avoids electrical conduction caused by the user accidentally touching the area between two adjacent sensing sections 13241, and further improves the safety of hair removal.

Figure 18:
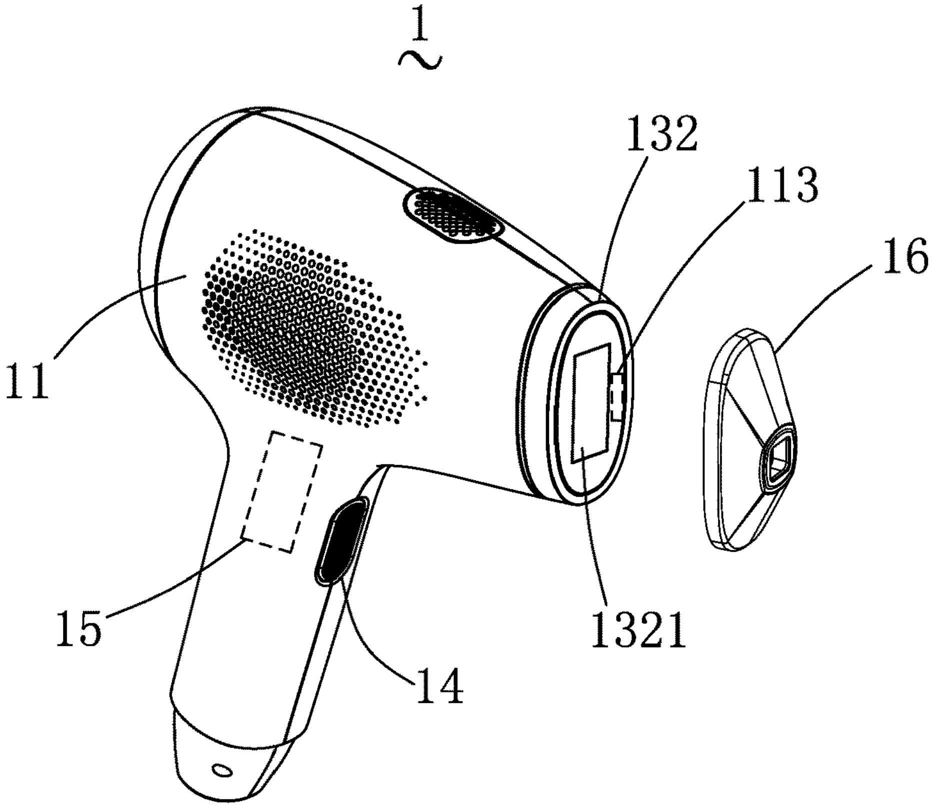
FIG. 18 is a schematic diagram of the portable hair removal apparatus provided with a converting head according to the first embodiment of the present disclosure.
Figure 19:
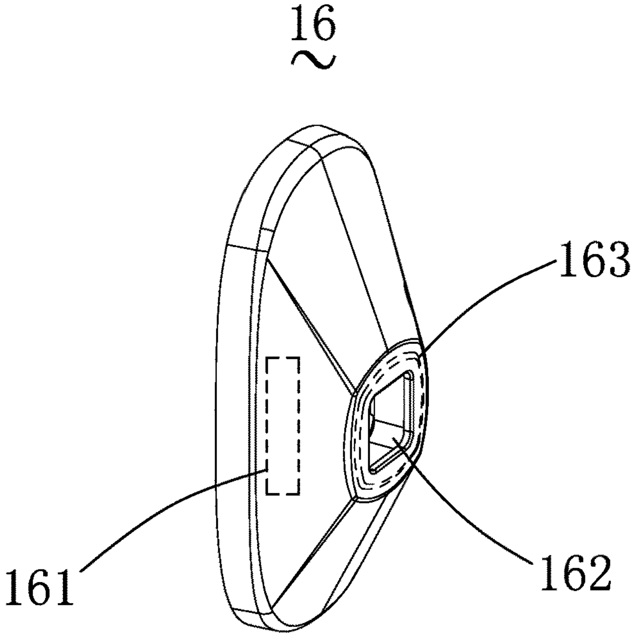
FIG. 19 is a schematic diagram of a second sensing member and a first magnetic member in the portable hair removal apparatus according to the first embodiment of the present disclosure.

Referring to FIG. 18 and FIG. 19, the portable hair removal apparatus 1 further includes a converting head 16. The converting head 16 is detachably connected to the contact portion 132. Specifically, the converting head 16 includes a first magnetic member 161, and the housing 11 includes a second magnetic member 113 corresponding to the contact member 1323. The first magnetic member 161 and the second magnetic member 113 are magnetically connected.

Specifically, the converting head 16 further includes a converting opening 162 and a second sensing member 163. The converting opening 162 is defined on the converting head 16 corresponding to the light-transmitting crystal 1321, whereby the light irradiated from the light-transmitting crystal 1321 is irradiated through the converting opening 162. The second sensing member 163 is sleeved on the peripheral side of the converting opening 162 and is configured to sense conductors. When the converting head 16 and the contact portion 132 are magnetically connected, the first sensing member 1324 and the second sensing member 163 are electrically conducted. That is, the converting head 16 senses the skin to be hair-removed through the second sensing member 163, to control the light emitting of the light-exit portion 131.

It can be understood that, the diameter of the converting opening 162 is different from that of the light-transmitting crystal 1321, so as to change the light-emitting area of the portable hair removal apparatus 1 and adapt to the user's hair removal requirements for different parts. For example, in this embodiment, the diameter of the converting opening 162 is smaller than that of the light-transmitting crystal 1321, whereby the converting head 16 can be adapted to the hair removal operation of smaller parts. Further, the surface of the converting head 16 has a sloped structure, that is, the converting head 16 forms a trapezoid-like structure from one side close to the contact portion 132 toward the opposite side, whereby the converting head 16 can reach relatively narrow parts of the user to perform hair removal, which improves the adaptability of the portable hair removal apparatus 1 to different hair removal environments.

It can be understood that, the converting head 16 includes a conversion filter (not shown) corresponding to the converting opening 162, and the light irradiated from the light-transmitting crystal 1321 passes through the conversion filter and then is irradiated as a preset light from the converting opening 162. For example, the user needs to remove hair of eyebrows, fingers and other parts, light of different wave bands can be irradiated through the conversion filter of the converting head 16, to adapt to the light requirements for hair removal of different parts.

Optionally, the converting opening 162 can be correspondingly provided with a light-transmitting member. The light-transmitting member is in contact with the skin to achieve cold compress effects.

Figure 20:
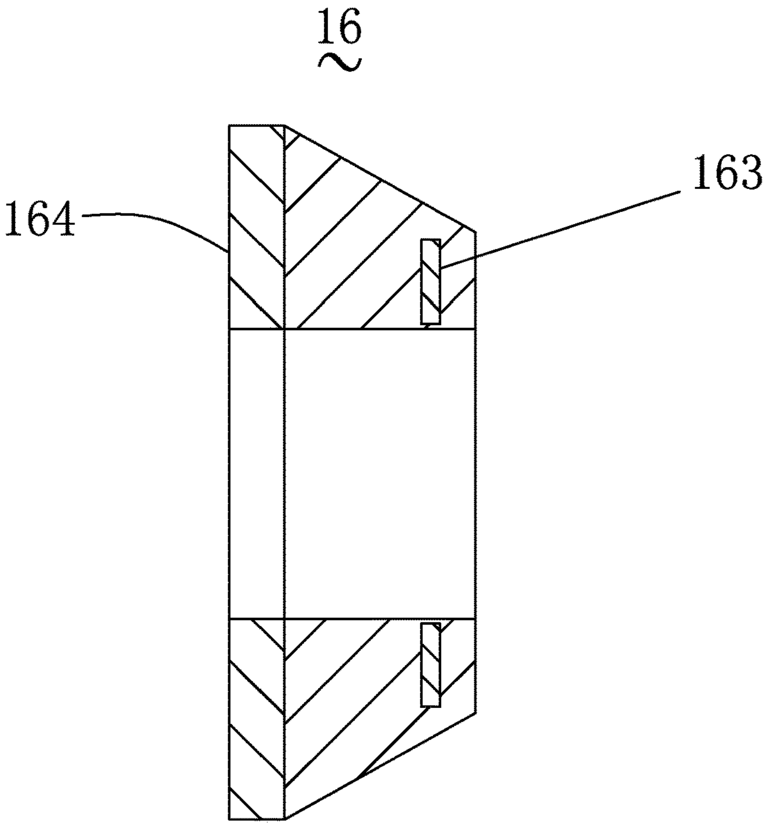
FIG. 20 is a sectional schematic diagram of the converting head in the portable hair removal apparatus according to the first embodiment of the present disclosure.

Referring to FIG. 18 and FIG. 20, the converting head 16 includes a metal surface 164 at a side close to the light-transmitting crystal 1321. The metal surface 164 can be exposed from the converting head 16 or disposed in the converting head 16. The metal surface 164 is connected to the second sensing member 163. Specifically, the metal surface 164 is connected to the second sensing member 163 by a metal member (not shown). When the converting head 16 is connected to the contact portion 132, the first sensing member 1324 senses the metal surface 164, and the conduction between the first sensing member 1324 and the second sensing member 163 is realized by the metal member.

It can be understood that, the materials of the metal surface 164 and the metal member include but not limited to one or more of aluminum, iron or copper.

Figure 21:
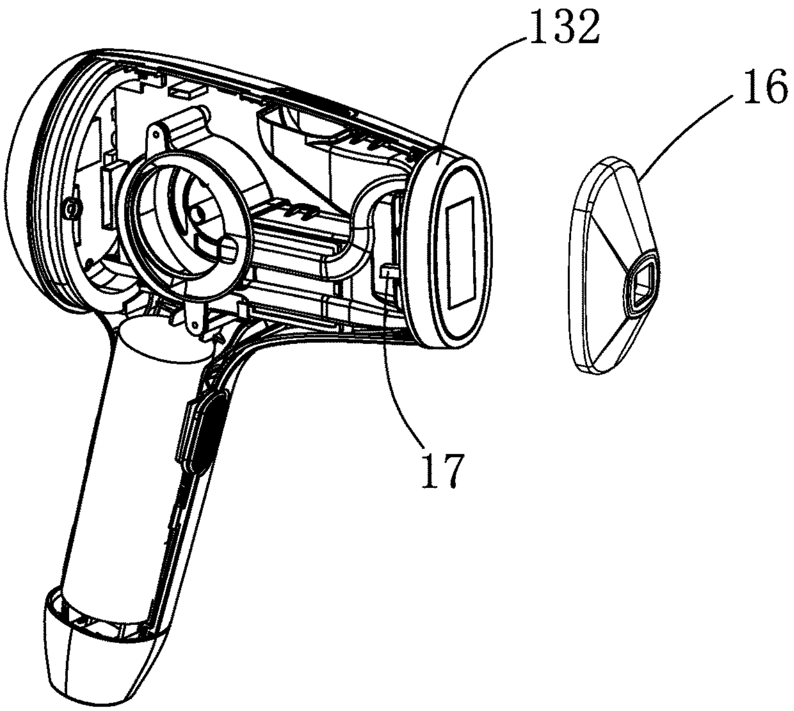
FIG. 21 is a schematic diagram of a Hall switch in the portable hair removal apparatus according to the first embodiment of the present disclosure.

Referring to FIG. 19 and FIG. 21, the portable hair removal apparatus 1 further includes a Hall switch 17. The Hall switch 17 is positioned at a side in the housing 11 close to the contact portion 132, and is electrically connected to the control module.

When the converting head 16 in magnetically connected to the contact portion 132, the Hall switch 17 senses the magnetic field of the first magnetic member 161, whereby the Hall switch 17 is closed, thereby controlling the light emitting of the portable hair removal apparatus 1 with the converting head 16.

Specifically, when the converting head 16 is magnetically connected to the contact portion 132, the first sensing member 1324 senses the first magnetic member 161, whereby the first sensing member 1324 is electrically conducted. That is, when the portable hair removal apparatus 1 is connected to the converting head 16, due to the conduction of the first sensing member 1324, the portable hair removal apparatus 1 can directly control the light emitting through the switch 14. And the Hall switch 17 is provided, whereby the Hall switch 17 reduces or resets the capacitance change value caused by the first magnetic member 161 to the first sensing member 1324, which prevents ineffective light emitting caused by wrong conduction of the first sensing element 1324 after the converting head 16 is connected.

Further, when the converting head 16 is magnetically connected to the contact portion 132, and when the converting head 16 senses the conductor, the first sensing member 1324 and the second sensing member 163 are electrically conducted. That is, the first sensing member 1324 send the capacitance change caused by the second sensing member 163 to the control module, and the control module controls the light emitting.

Figure 22:
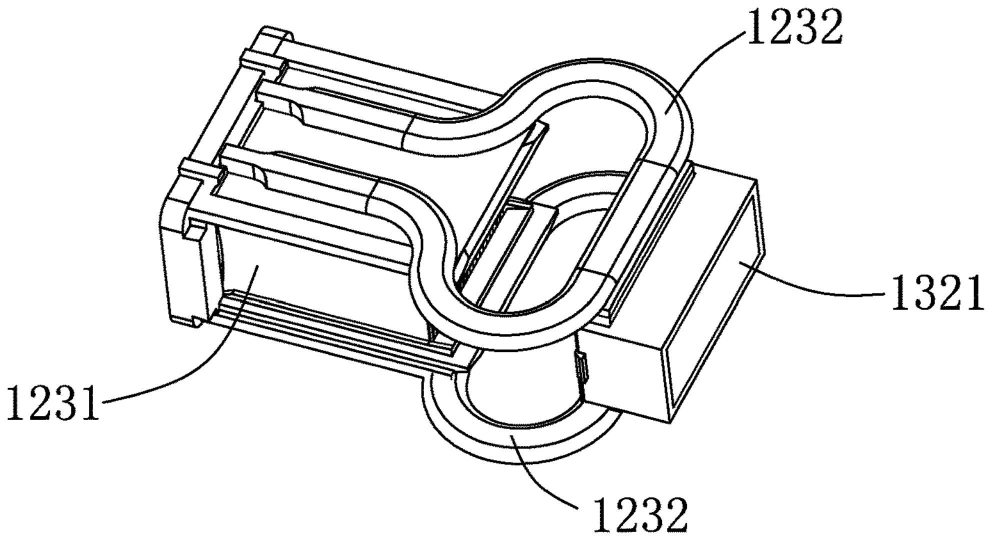
FIG. 22 is a schematic diagram of a heat conduction member disposed at a side of a light-transmitting crystal in the portable hair removal apparatus according to the first embodiment of the present disclosure.
Figure 23:
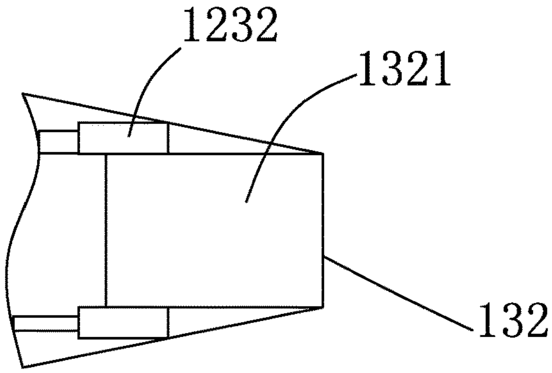
FIG. 23 is a schematic diagram of the protruding light-transmitting crystal in the portable hair removal apparatus according to the first embodiment of the present disclosure.

Referring to FIG. 22 and FIG. 23, as an embodiment, one end of the heat conduction member 1232 is connected to an end of a side of the light-transmitting crystal 1321 close to the heat dissipation member 1231, the other end of the heat conduction member 1232 is connected to the heat dissipation member 1231. That is, the heat conduction member 1232 is disposed on the end of the side of the light-transmitting crystal 1321 away from the light-emitting direction, whereby the light-transmitting crystal 1321 can protrude out of the housing 11 (as shown in FIG. 23), which enables the size of the contact portion 132 to be smaller, and increases the area ratio of the light-transmitting crystal 1321 on the side surface of the contact portion 132 in contact with the skin. Therefore, during hair removal, the smaller size of the contact portion 132 facilitates the user to observe the hair removal situation in real time without removing the apparatus to observe, which avoids the problem of inconvenient observation and operation caused by the contact portion 132 being too large, and improves the user experience.

It can be understood that, the number of the heat conduction member 1232 can be one, two, three or more, as long as the end of each heat conduction member 1232 is connected to the end of the side of the light-transmitting crystal 1321 close to the heat dissipation member 1231, to reduce the size of the contact portion 132, which is not limited herein.

It can be understood that, the heat conduction member 1232 is connected to the light-transmitting crystal 1321 in a direct contact manner, or a indirect manner. For example, the heat conduction member 1232 can be connected to the light-transmitting crystal 1321 through the semiconductor refrigeration sheet 125, which will not be repeated here.

As an embodiment, the number of the heat conduction member 1232 is two, and the two heat conduction members 1232 are respectively disposed at opposite sides of the heat dissipation member 1231. Each heat conduction member 1232 is connected to the same side of the heat dissipation member 1231 and the light-transmitting crystal 1321. That is, the condensing section 12321 and the heat dissipating section 12322 of each heat conduction member 1232 are disposed coplanarly. One heat conduction member 1232 is disposed at one side of the heat dissipation member 1231, the other heat conduction member 1232 is disposed at the other side of the heat dissipation member 1231. The two heat conduction members 1232 are respectively disposed at the opposite sides of the heat dissipation member 1231, whereby the heat dissipation member 1231 can dissipate heat from the two heat conduction members more evenly, which improves the heat dissipation efficiency.

Figure 24:
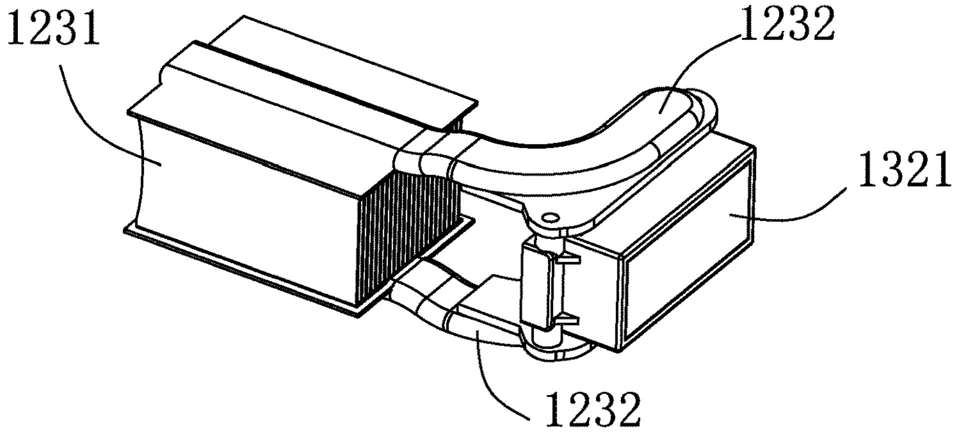
FIG. 24 is a schematic diagram of the L-shaped or L-like heat conduction member in the portable hair removal apparatus according to the first embodiment of the present disclosure.

Optionally, referring to FIG. 22 and FIG. 24, the heat conduction member 1232 is a U-shaped or imitated U-shaped heat conduction member (the heat conduction member 1232 as shown in FIG. 22), or the heat conduction member 1232 is an L-shaped or imitated L-shaped heat conduction member (the heat conduction member 1232 as shown in FIG. 24), as long as the heat conduction member 1232 is respectively disposed at the opposite sides of the heat dissipation member 1231. The number of the heat conduction member 1232 can also be one, three, four, five or more, as long as the heat conduction member 1232 is respectively disposed at the opposite sides of the heat dissipation member 1231, which is not limited herein. For example, when the number of the heat conduction member 1232 is one, the single heat conduction member 1232 is disposed at one side of the heat dissipation member 1231.

Figure 25:
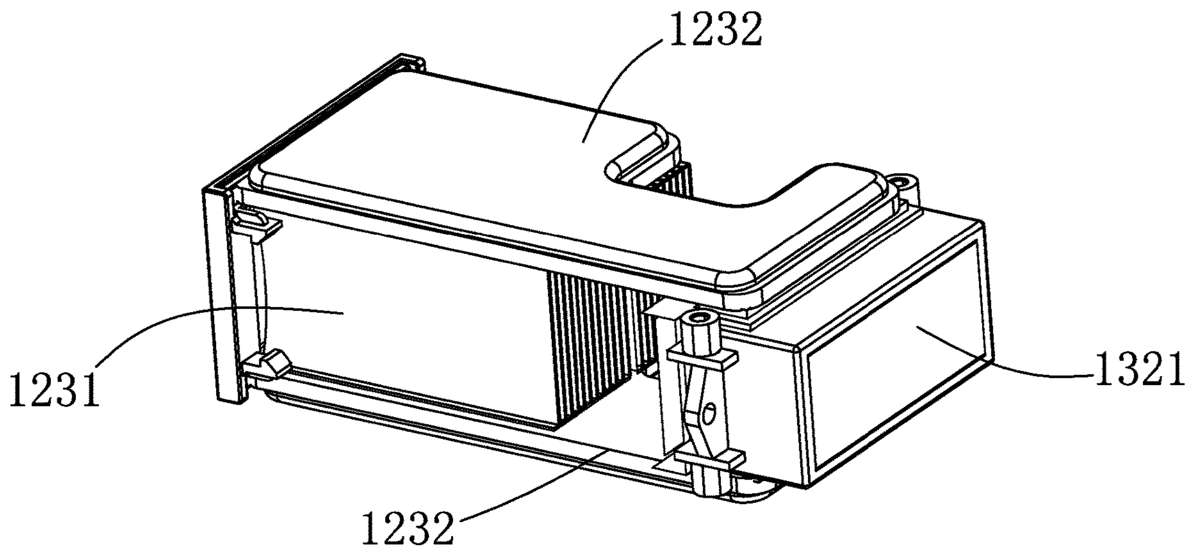
FIG. 25 is a schematic diagram of the heat conduction member being a vapor chamber in the portable hair removal apparatus according to the first embodiment of the present disclosure.

Referring to FIG. 25, as another embodiment, when the heat conduction member 1232 is a vapor chamber, one end of the two heat conduction members 1232 covers the opposite sides of the heat dissipation member 1231, the other end is connected to the light-transmitting crystal 1321, so as to improve the heat dissipation efficiency. The number of the vapor chamber can also be one, and the single vapor chamber is disposed at one side of the heat dissipation member 1231.

The foregoing descriptions of the embodiments according to the present disclosure should not be construed as limiting the scope of the disclosure but as merely providing illustrations of some of the preferred embodiments thereof. Thus the scope of the disclosure should be determined by the appended claims and their legal equivalents. Furthermore, it will be apparent to those skilled in the art that various modifications, equivalents and improvements can be made herein within the scope of the disclosure.

The invention claimed is:

1. A portable hair removal apparatus, comprising a hair removal mechanism for contacting the skin to remove hair, and a housing, wherein the housing defines an accommodating space, and the hair removal mechanism is accommodated therein;

the hair removal mechanism comprising a light-exit portion for emitting light irradiated to the hair to be removed, and a contact portion, the contact portion exposed from the accommodating space and disposed in a light-emitting direction of the light-exit portion;

the contact portion comprising a light-transmitting crystal disposed in the light-emitting direction of the light-exit portion, and the light-transmitting crystal being in contact with the skin;

a hollow spacer element is positioned between the light-exit portion and the light-transmitting crystal and the hollow spacer element is configured to seal the area between the light-exit portion and the light-transmitting crystal and prevent the air at the opposite sides of the light-exit portion and/or the light-transmitting crystal from liquefying.

2. The portable hair removal apparatus according to claim 1, wherein the portable hair removal apparatus further comprises a heat dissipation mechanism accommodated in the accommodating space;

the heat dissipation mechanism comprising a blowing member, a heat dissipation channel and a heat dissipation assembly, the heat dissipation assembly disposed between the blowing member and the heat dissipation channel, or the heat dissipation assembly disposed at a side of the heat dissipation channel close to the blowing member.

3. The portable hair removal apparatus according to claim 2, wherein the housing is provided with a first vent and a second vent which are communicated with the accommodating space, and the blowing member is disposed corresponding to the first vent;

the heat dissipation assembly comprising a heat dissipation member and at least one heat conduction member, the heat dissipation member disposed between the blowing member and the heat dissipation channel, or the heat dissipation member disposed at the side of the heat dissipation channel close to the blowing member; one end of the heat dissipation channel communicated with the at least one second vent, the other end thereof connected to the heat dissipation member; one end of the at least one heat conduction member being in contact with the heat dissipation member, the other end thereof being in contact with at least one side of the hair removal mechanism;

the blowing member pushing air flow between the first vent and the at least one second vent.

4. The portable hair removal apparatus according to claim 3, wherein the blowing member comprises a first air inlet and a first air outlet, the first air inlet is disposed corresponding to the first vent, and the first air outlet is disposed corresponding to the heat dissipation member;

the heat dissipation channel comprising a second air inlet and at least one second air outlet, the second air inlet disposed corresponding to the heat dissipation member, the at least one second air outlet communicated with the second vent.

5. The portable hair removal apparatus according to claim 3, wherein the heat dissipation mechanism further comprises a sealing element sleeved on a side of the heat dissipation member close to the heat conduction member, to seal a gap between the heat dissipation channel and the heat dissipation member.

6. The portable hair removal apparatus according to claim 3, wherein the heat conduction member comprises a condensing section and an opposite heat dissipating section, the condensing section being connected to the heat dissipation member, and the heat dissipating section being connected to at least one side of the light-transmitting crystal;

the condensing section connected to a side of the light-transmitting crystal close to the heat dissipation member.

7. The portable hair removal apparatus according to claim 6, wherein the number of the heat conduction member is at least two, the at least two heat conduction members are respectively disposed at opposite sides of the heat dissipation member, and the heat conduction member is U-shaped or imitated U-shaped.

8. The portable hair removal apparatus according to claim 3, wherein the heat dissipation mechanism further comprises at least one semiconductor refrigeration sheet disposed between the light-transmitting crystal and the heat conduction member;

the at least one semiconductor refrigeration sheet comprising a refrigeration surface and an opposite heat dissipation surface, the refrigeration surface being in contact with the side of the light-transmitting crystal, and the heat dissipation surface being in contact with the heat dissipating section;

the refrigeration surface being in contact with at least one side corresponding to a wide side or a long side of the light-transmitting crystal.

9. The portable hair removal apparatus according to claim 1, wherein the contact portion comprises a collar sleeved on a side of the housing, and a first sensing member positioned in the collar for sensing conductors.

10. The portable hair removal apparatus according to claim 9, wherein the contact portion further comprises a limiting member and a contact member, the limiting member being sleeved on an outer side of the light-transmitting crystal to fasten the light-transmitting crystal, and the contact portion being disposed on the outer side of the light-transmitting crystal to cover an area between the collar and the light-transmitting crystal;

at least one side of the limiting member and/or the contact member close to the light-transmitting crystal provided with a limiting portion protruding toward the light-transmitting crystal, and the light-transmitting crystal defining a groove corresponding to and matching the limiting portion.

11. The portable hair removal apparatus according to claim 9, wherein the portable hair removal apparatus further comprises a control module electrically connected to the light-exit portion;

the first sensing member comprising at least two sensing sections, the at least two sensing sections positioned in the collar, and each sensing section electrically connected to the control module;

the collar formed on a peripheral side of the at least two sensing sections;

the distance between each sensing section and a side of the collar away from the light-exit portion being 0.2 mm-2 mm;

the distance between two adjacent sensing sections being 3 mm-30 mm.

12. The portable hair removal apparatus according to claim 9, wherein the light-exit portion comprises a light tube, an optical filter and a reflective member which are disposed in the heat dissipation channel, and the heat dissipation channel being provided with a light-exit opening at a side close to the contact portion;

the light tube positioned in the heat dissipation channel, for emitting light irradiated to the hair to be removed through the light-exit opening;

the optical filter disposed in the light-emitting direction of the light tube, and the reflective member disposed in a direction opposite to the light-emitting direction.

13. The portable hair removal apparatus according to claim 12, wherein the portable hair removal apparatus further comprises a converting head detachably connected to the contact portion;

the converting head comprising a converting opening corresponding to the light-exit opening, the diameter of the converting opening being different from that of the light-exit opening;

the converting head further comprising a second sensing member sleeved on a peripheral side of the light-exit opening, for sensing the conductors;

the converting head comprising a metal surface at a side close to the light-transmitting crystal, and the metal surface electrically connected to the second sensing member;

when the converting head is connected to the hair removal mechanism, the first sensing member sensing the metal surface.

14. The portable hair removal apparatus according to claim 13, wherein the portable hair removal apparatus further comprises a Hall switch positioned at a side in the housing close to the hair removal mechanism, and the converting head comprising a first magnetic member;

when the converting head is connected to the hair removal mechanism, the Hall switch sensing the first magnetic member to control light emitting of the hair removal mechanism.

* * * * *